US008660831B2

(12) United States Patent
Wang et al.

(10) Patent No.: US 8,660,831 B2
(45) Date of Patent: Feb. 25, 2014

(54) EXTENSION OF COSMO-SAC SOLVATION MODEL FOR ELECTROLYTES

(75) Inventors: Shu Wang, Acton, MA (US); Yuhua Song, Somerville, MA (US); Chau-Chyun Chen, Lexington, MA (US)

(73) Assignee: Aspen Technology, Inc., Burlington, MA (US)

( * ) Notice: Subject to any disclaimer, the term of this patent is extended or adjusted under 35 U.S.C. 154(b) by 310 days.

(21) Appl. No.: 13/271,455

(22) Filed: Oct. 12, 2011

(65) Prior Publication Data

US 2012/0095736 A1 Apr. 19, 2012

Related U.S. Application Data

(60) Provisional application No. 61/392,549, filed on Oct. 13, 2010.

(51) Int. Cl.
*G06G 7/58* (2006.01)

(52) U.S. Cl.
USPC .................................. 703/12; 703/11; 703/2

(58) Field of Classification Search
USPC ................ 703/2, 11, 12; 702/19, 25; 436/161
See application file for complete search history.

(56) References Cited

U.S. PATENT DOCUMENTS

| | | | |
|---|---|---|---|
| 2005/0187748 A1* | 8/2005 | Chen et al. | 703/11 |
| 2006/0031053 A1* | 2/2006 | Chen et al. | 703/12 |
| 2007/0112526 A1* | 5/2007 | Chen | 702/19 |
| 2008/0076187 A1* | 3/2008 | Chen | 436/161 |
| 2010/0114542 A1* | 5/2010 | Chen et al. | 703/2 |
| 2011/0257947 A1* | 10/2011 | Chen | 703/2 |
| 2013/0024133 A1* | 1/2013 | Chen | 702/25 |
| 2013/0035923 A1* | 2/2013 | Chen et al. | 703/12 |

OTHER PUBLICATIONS

Notification of Transmittal of the International Search Report and the Written Opinion of the International Searching Authority, or the Declaration, International Application No. PCT/US2011/055886, Mailing Date: Jan. 31, 2012.

Wang, S., "Thermodynamic Properties Predictions Using the COSMO-SAC Solvation Method", Unpublished PhD dissertation, University of Delaware (2007).

Chen, Ch-Ch, et al., "Toward Development of activity coefficient models for process and product design of complex chemical systems", *Fluid Phase Equilibria Elsevier*, 241(1-2): 103-112 (2006).

Chen, Ch-Ch, et al., "Extension of Nonrandom Two-Liquid Segment Activity Coefficient Model for Electrolytes," *Ind. Eng. Chem. Res.*, 44(23): 8909-8921 (2005).

Song, Y., et al., "Symmetric Electrolyte Nonrandom Two-Liquid Activity Coeffecient Model", *Ind. Eng. Chem. Res.*, 48(16): 7788-7797 (2009).

(Continued)

*Primary Examiner* — Kandasamy Thangavelu
(74) *Attorney, Agent, or Firm* — Hamilton, Brook, Smith & Reynolds, P.C.

(57) ABSTRACT

An extension of COSMO-SAC to electrolytes (eCOSMO-SAC) combines the COSMO-SAC term for short range molecule-molecule, molecule-ion and ion-ion interactions with the extended symmetric Pitzer-Debye-Hückel term for long range ion-ion interactions. The extension recognizes that like-ion repulsion and local electroneutrality govern the surface segment contacts, and introduces a dual sigma profile concept for electrolyte systems. The eCOSMO-SAC formulation predicts activity coefficients of several representative electrolyte systems.

36 Claims, 21 Drawing Sheets

(56) References Cited

OTHER PUBLICATIONS

Hsieh, M-T., et al., "A Predictive Model for the Excess Gibbs Free Energy of Fully Dissociated Electrolyte Solutions", *AIChE Journal*, 57(4): 1061-1074 (2010).

Liu, Y., et al., "Successfully Simulating Electrolyte Systems", *Chemical Engineering Progress, American Institute of Chemical Engineers*, pp. 25-42 (1999).

Wang, S., et al., "Extension of COSMO-Sac Solvation Model for Electrolytes", *Ind. Eng. Chem. Res.*, 50(1): 176-187 (2011).

Notification Concerning Transmittal of the International Preliminary Report on Patentability for International Application No.: PCT/US2011/055886, "Extension of COSMO-SAC Solvation Model for Electrolytes," Mailing Date: Apr. 25, 2013, 7 pages.

Pitzer, K.S., "Thermodynamics of Electrolytes, I. Theoretical Basis and General Equations", *J. Phys. Chem.*, 1973, 77, pp. 268-277.

Chen, C.-C., et al., "Local Composition Model for Excess Gibbs Energy of Electrolyte Systems, Part I: Single Solvent, Single Completely Dissociated Electrolyte Systems", *AIChE J.*, 1982, 28, pp. 588-596.

Chen, C.-C., et al., "Generalized Electrolyte NRTL Model for Mixed-Solvent Electrolyte Systems", *AIChE J.*, 2004, 50, pp. 1928-1941.

Song, Y., et al., "Symmetric Nonrandom Two-Liquid Segment Activity Coefficient Model for Electrolytes", *Ind. Eng. Chem. Res.*, 2009, 48, pp. 5522-5529.

Lin, S.T., et al., "A Priori Phase Equilibrium Prediction from a Segment Contribution Solvation Model", *Ind. Eng. Chem. Res.*, 2002, 41, pp. 899-913.

Mullins, E., et al., "Sigma-Profile Database for Using COSMO-Based Thermodynamic Methods", *Ind. Eng. Chem. Res.*, 2006, 45, pp. 4389-4415.

Klamt, A., "COSMO-RS From Quantum Chemistry to Fluid Phase Thermodynamics and Drug Design", Elsevier, Amsterdam, pp. 127-136, 2005.

Wang, S., et al., "Refinement of COSMO-SAC and the Applications", *Ind. Eng. Chem. Res.*, 2007, 46, pp. 7275-7288.

\* cited by examiner

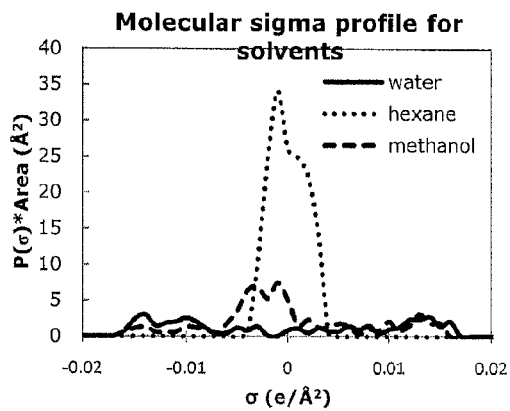
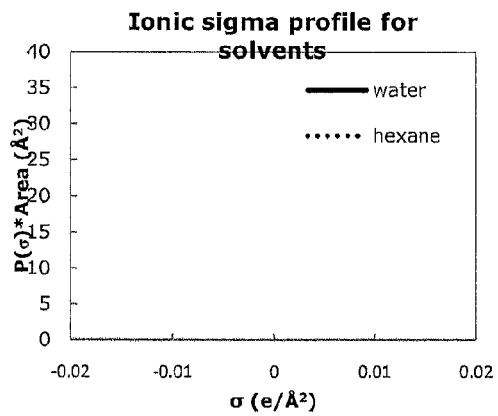
FIG. 2A
FIG. 2B
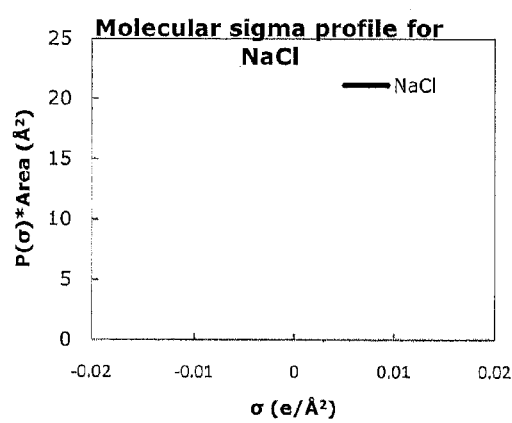
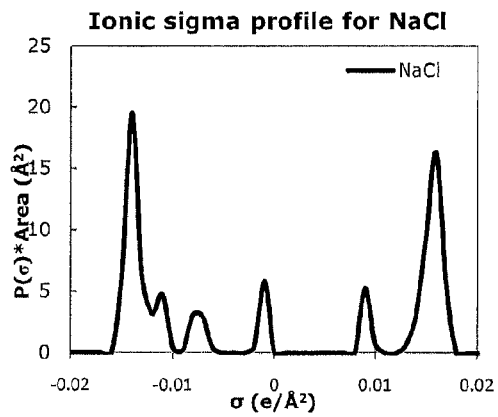
FIG. 2C
FIG. 2D

EXTENSION OF COSMO-SAC SOLVATION MODEL FOR ELECTROLYTES

RELATED APPLICATION(S)

This application claims the benefit of U.S. Provisional Application No. 61/392,549, filed on Oct. 13, 2010. The entire teachings of the above application(s) are incorporated herein by reference.

BACKGROUND OF THE INVENTION

Electrolyte solutions are ubiquitous in chemical process industries. Current efforts in the development of activity coefficient-based electrolyte thermodynamic models largely follow two main tracks: 1) virial expansion empirical expressions represented by the Pitzer equation and 2) local composition semi-empirical expressions represented by the electrolyte NRTL model. See Pitzer, K. S., Thermodynamics of Electrolytes, I. Theoretical Basis and General Equations, *J. Phys. Chem.*, 1973, 77, 268-277; Song, Y., Chen, C.-C., Symmetric Electrolyte Nonrandom Two-Liquid Activity Coefficient Model, *Ind. Eng. Chem. Res.*, 2009, 48, 7788-7797; Chen, C.-C., Britt, H. I., Boston, J. F., Evans, L. B., Local Composition Model for Excess Gibbs Energy of Electrolyte Systems, Part I: Single Solvent, Single Completely Dissociated Electrolyte Systems, *AIChE J.*, 1982, 28, 588-596; Chen, C.-C., Song, Y., Generalized Electrolyte NRTL Model for Mixed-Solvent Electrolyte Systems, *AIChE J.*, 2004, 50, 1928-1941. These models provide sound thermodynamic frameworks to quantitatively correlate available thermodynamic data for interpolation and extrapolation.

More recently a segment-based electrolyte activity coefficient model has been proposed as a correlative and predictive thermodynamic framework. See Chen, C.-C., Song, Y., Extension of Non-Random Two-Liquid Segment Activity Coefficient Model for Electrolytes, *Ind. Eng. Chem. Res.*, 2005, 44, 8909-8921; Song, Y., Chen, C.-C., Symmetric Nonrandom Two-Liquid Segment Activity Coefficient Model for Electrolytes, *Ind. Eng. Chem. Res.*, 2009, 48, 5522-5529. The model requires component-specific "conceptual segment" parameters that can be determined from correlating experimental data in a few representative systems. The model can then be used to qualitatively predict phase behavior of any electrolyte systems as long as the conceptual segment parameters are known for the molecules and electrolytes.

COSMO-based activity coefficient models such as COSMO-SAC (Conductor-like screening model-segment activity coefficient) and COSMO-RS have been shown to be relatively successful predictive models for molecular systems. See Lin, S. T., Sandler, S. I., A Priori Phase Equilibrium Prediction from a Segment Contribution Solvation Model. *Ind. Eng. Chem. Res.*, 2002, 41, 899-913; Mullins, E., Oldland, R., Liu, Y. A., Wang, S., Sandler, S. I., Chen, C.-C., Zwolak, M., Seavey, K. C., Sigma-Profile Database for Using COSMO-Based Thermodynamic Methods, *Ind. Eng. Chem. Res.*, 2006, 45, 4389-4415; Klamt, A., COSMO-RS From Quantum Chemistry to Fluid Phase Thermodynamics and Drug Design, Elsevier, Amsterdam, 2005. The COSMO-SAC solvation model uses the "screening charge density" or "sigma profile" of the molecular surface calculated from quantum chemistry as a descriptor to compute the activity coefficient of each component in mixtures. These models are capable of reasonably robust predictions for thermodynamic properties of thousands of components and their mixtures without any experimental data. See Wang, S, Sandler, S. I., Chen, C. C., Refinement of COSMO-SAC and the Applications, *Ind. Eng. Chem. Res.*, 2007, 46, 7275-7288. Although COSMO-based models were originally developed for molecular systems, they were later successfully applied to molecular species in ionic liquids. See Klamt, A., COSMO-RS From Quantum Chemistry to Fluid Phase Thermodynamics and Drug Design, Elsevier, Amsterdam, 2005; Wang, S, Thermodynamic Properties Predictions using the COSMO-SAC Solvation method, Ph.D. thesis, University of Delaware, 2007. The success suggests that the COSMO-SAC formulation provides adequate representation of short-range molecule-molecule interactions and, to a certain extent, the short-range molecule-ion interactions.

There is, however, a continuing need for improved predictive electrolyte thermodynamic models capable of an adequate representation for the short range ion-ion interactions.

SUMMARY OF THE INVENTION

The invention generally is directed to a method of modeling at least one physical property of a mixture of at least two chemical species that includes at least one electrolyte dissolved in one or more solvents.

In one embodiment, a method of modeling at least one physical property of a mixture of at least two chemical species that includes at least one electrolyte dissolved in one or more solvents using a modeler includes the computer implemented step of generating an ionic charge density (sigma) profile and a molecular charge density (sigma) profile for each electrolyte and each solvent. The method further includes computing, using the generated sigma profiles, the short range interactions including: (i) calculating molecule-molecule interactions by using the molecular sigma profile of each electrolyte and each solvent, (ii) calculating molecule-ion interactions by using the molecular sigma profile of each electrolyte and each solvent and the ionic sigma profile of each electrolyte and each solvent, and including repulsion and attraction energy terms, and (iii) calculating ion-ion interactions by using the ionic sigma profiles of each electrolyte and each solvent, and including repulsion and attraction energy terms. The method then includes: (a) calculating an activity coefficient for each respective cation and anion of each electrolyte and an activity coefficient for each solvent by combining a long-range interaction contribution with the computed short-range interaction contribution, (b) using the calculated activity coefficients to compute at least one physical property of the mixture including any one of vapor pressure, solubility, boiling point, freezing point, octanol/water partition coefficient, mean ionic activity coefficient, osmotic coefficient, or a combination thereof, and (c) analyzing the computed physical property using the modeler. The analysis forms a model of the at least one physical property of the mixture, followed by the modeler outputting the formed model to a computer display monitor. Generating the ionic and molecular sigma profiles for each electrolyte and each solvent includes computing a sigma profile for each electrolyte and each solvent, the sigma profile including charge density segments associated with charged atoms and charge density segments associated with neutral atoms.

In another embodiment, a computer apparatus for modeling at least one physical property of a mixture of at least two chemical species that includes at least one electrolyte dissolved in one or more solvents includes: (a) a digital processor member having an ionic charge density (sigma) profile and a molecular charge density (sigma) profile for each electrolyte and each solvent, and (b) a processing unit operatively coupled to the digital processor member. The processing unit includes a modeler modeling physical properties of mixtures. The processing unit uses the sigma profiles to compute short-range interactions, including: (i) calculating molecule-molecule interactions by using the molecular sigma profile of each electrolyte and the molecular sigma profile of each solvent, (ii) calculating molecule-ion interactions by using the molecular sigma profile of each electrolyte and each solvent and the ionic sigma profile of each electrolyte and each solvent, and including repulsion and attraction energy terms, and (iii) calculating ion-ion interactions by using the ionic sigma profiles of each electrolyte and each solvent, and including repulsion and attraction energy terms. The processing unit then calculates an activity coefficient for each respective cation and anion of each electrolyte and an activity coefficient for each solvent by combining a long-range interaction contribution with the computed short-range interaction contribution, and uses the calculated activity coefficients to compute at least one physical property of the mixture. The computed physical property can include any one of vapor pressure, solubility, boiling point, freezing point, octanol/water partition coefficient, mean ionic activity coefficient, osmotic coefficient, or a combination thereof. The processing unit analyzes the computed physical property using the modeler, the analysis forming a model of the at least one physical property of the mixture. The computer apparatus further includes an output module coupled to receive the formed model and to provide an indication of the formed model as output.

This invention has many advantages, including improved predictions of activity coefficients for electrolyte systems.

BRIEF DESCRIPTION OF THE DRAWINGS

The foregoing will be apparent from the following more particular description of example embodiments of the invention, as illustrated in the accompanying drawings in which like reference characters refer to the same parts throughout the different views.

The drawings are not necessarily to scale, emphasis instead being placed upon illustrating embodiments of the present invention.

FIGS. 2A-D are graphs of molecular and ionic sigma profiles for water, hexane and methanol solvents and for NaCl electrolyte.

DETAILED DESCRIPTION OF THE INVENTION

Figure 1:
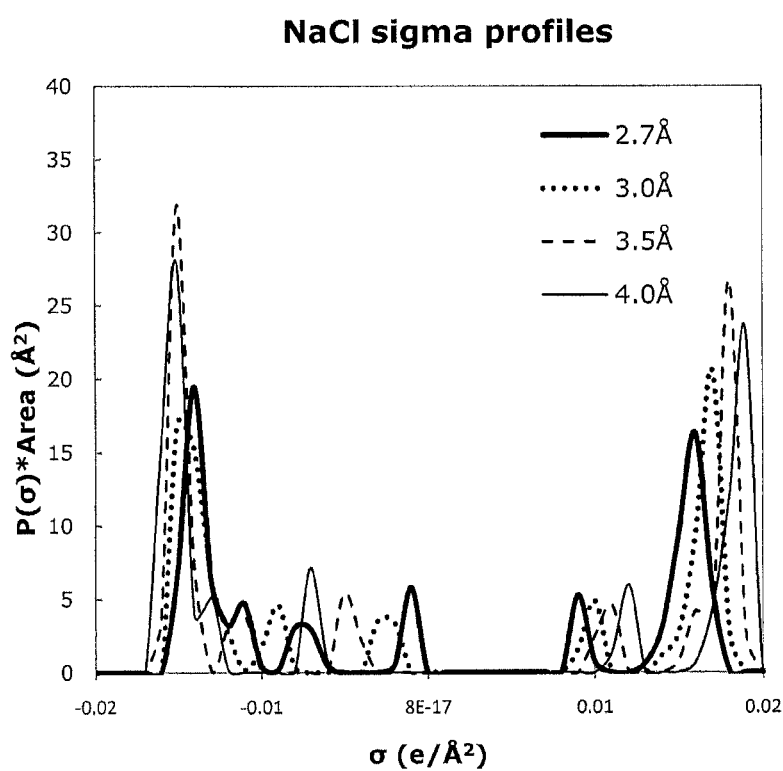
FIG. 1 is a graph of NaCl sigma profiles with different distances between $Na^+$ and $Cl^-$.

Except in the dilute electrolyte concentration region, short range interactions are known to play the dominant role in the phase behavior of electrolyte solutions. See Chen, C.-C., Britt, H. I., Boston, J. F., Evans, L. B., Local Composition Model for Excess Gibbs Energy of Electrolyte Systems, Part I: Single Solvent, Single Completely Dissociated Electrolyte Systems, *AIChE J.*, 1982, 28, 588-596; Mock, B., Evans, L. B., Chen, C.-C., Thermodynamic Representation of Phase Equilibria of Mixed-Solvent Electrolyte Systems, *AIChE J.*, 1986, 32, 1655-1664. In the present invention, an extension of COSMO-SAC to electrolytes combines the COSMO-SAC term for short-range molecule-molecule, molecule-ion and ion-ion interactions with the extended symmetric Pitzer-Debye-Hückel term for long-range ion-ion interactions. The extension recognizes that like-ion repulsion and local electroneutrality govern the surface segment contacts, and introduces a dual sigma profile concept for electrolyte systems.

The results of the extension of COSMO-SAC to describe the complex behavior of electrolytes are compared below to those obtained using existing successful correlative models, as examples of useful references. Specifically, the predictions of eCOSMO-SAC for a few representative electrolyte systems were compared with those calculated from eNRTL, a widely-practiced correlative model for electrolyte activity coefficients. See Song, Y., Chen, C.-C., Symmetric Electrolyte Nonrandom Two-Liquid Activity Coefficient Model, *Ind. Eng. Chem. Res.*, 2009, 48, 7788-7797. In addition, the sensitivities of the model predictions to the various model parameters are examined. Moreover, the general characteristics of eCOSMO-SAC model predictions are compared with experimental data for selected electrolyte systems including aqueous single electrolytes, aqueous multielectrolytes, and single electrolytes in mixed solvents.

COSMO-SAC

There are many references for the COSMO-SAC model. See Lin, S. T., Sandler, S. I., *A Priori Phase Equilibrium Prediction from a Segment Contribution Solvation Model*, *Ind. Eng. Chem. Res.*, 2002, 41, 899-913; Mullins, E., Oldland, R., Liu, Y. A., Wang, S., Sandler, S. I., Chen, C.-C., Zwolak, M., Seavey, K. C., Sigma-Profile Database for Using COSMO-Based Thermodynamic Methods, *Ind. Eng. Chem. Res.*, 2006, 45, 4389-4415, and references cited therein. A brief summary of COSMO-SAC is given here as a basis for extension to electrolytes.

For molecular systems, the activity coefficient of species i in a solution S can be computed from Eq. (1):

$$\ln \gamma_i^{COSMO-SAC} = \frac{\Delta G_{i/S}^{*res} - \Delta G_{i/i}^{*res}}{RT} + \ln \gamma_i^{SG} \quad (1)$$

The restoring free energy of the solute i in solution S is:

$$\frac{\Delta G_{i/S}^{*res}}{RT} = \sum_{\sigma_m}\left[n_i(\sigma_m)\frac{\Delta G_{\sigma_m/S}^{*res}}{RT}\right] = n_i \sum_{\sigma_m} p_i(\sigma_m)\ln\Gamma_S(\sigma_m) \quad (2)$$

$$n_i = \sum_{\sigma} n_i(\sigma) \quad (3)$$

$$p_i(\sigma) = \frac{n_i(\sigma)}{n_i} \quad (4)$$

where $n_i(\sigma)$ is the number of segments, for the solute i, with a discretized surface charge density $\sigma$, $\Delta G_{\sigma_m/S}^{*res} = RT \ln \Gamma_S(\sigma_m)$ is the free energy required to add a segment with charge density $\sigma_m$ to a fixed position in the solution S, and $\Gamma_S(\sigma_m)$ is the activity coefficient for a segment with charge density $\sigma_m$ in the solution S.

Similarly, the restoring free energy of the solute i in its pure liquid is:

$$\frac{\Delta G_{i/i}^{*res}}{RT} = \sum_{\sigma_m}\left[n_i(\sigma_m)\frac{\Delta G_{\sigma_m/i}^{*res}}{RT}\right] = n_i \sum_{\sigma_m} p_i(\sigma_m)\ln\Gamma_i(\sigma_m) \quad (5)$$

where $\sigma$, $\Delta G_{\sigma_m/i}^{*res} = RT \ln \Gamma_i(\sigma_m)$ is the free energy required to add a segment with charge density $\sigma_m$ to a fixed position in the pure liquid i.

The activity coefficient of species i can be expressed as:

$$\ln \gamma_i^{COSMO-SAC} = n_i \sum_{\sigma_m} p_i(\sigma_m)[\ln\Gamma_S(\sigma_m) - \ln\Gamma_i(\sigma_m)] + \ln \gamma_i^{SG} \quad (6)$$

where $\ln \gamma_i^{SG}$ is the Staverman-Guggenheim combinatorial term based on lattice theory. Here is the segment activity coefficient in COSMO-SAC:

$$\ln\Gamma_S(\sigma_m) = -\ln\left\{\sum_{\sigma_n} p_S(\sigma_n)\Gamma_S(\sigma_n)\exp\left[\frac{-\Delta W(\sigma_m, \sigma_n)}{RT}\right]\right\} \quad (7)$$

$$\ln\Gamma_i(\sigma_m) = -\ln\left\{\sum_{\sigma_n} p_i(\sigma_n)\Gamma_i(\sigma_n)\exp\left[\frac{-\Delta W(\sigma_m, \sigma_n)}{RT}\right]\right\} \quad (8)$$

The exchange energy, $\Delta W(\sigma_m, \sigma_n)$, is:

$$\Delta W(\sigma_m, \sigma_n) = E_{misfit}(\sigma_m, \sigma_n) + E_{h-bond}(\sigma_m, \sigma_n) \quad (9)$$

The misfit energy is due to differences or misfit between a pair of segments $\sigma_m$, $\sigma_n$ and a pair of ideal segments with exactly opposite polarities:

$$E_{misfit}(\sigma_m, \sigma_n) = \frac{f_{pol}\alpha}{2}(\sigma_m + \sigma_n)^2 \quad (10)$$

where $f_{pol}$ is the polarization factor and $\alpha$ is the coefficient constant. Note that the misfit energy is always positive, i.e., repulsive, as the contribution is to increase the total exchange energy.

The hydrogen bonding energy is due to the hydrogen-bond interaction. This extra energy is required because of the electron interaction between a highly polarized segment with negative charge (charge density less than the cutoff value–$\sigma_{hb}$, defined as an hb-donor segment) and a highly polarized segment with positive charge (charge density greater than the cutoff value $\sigma_{hb}$, defined as an hb-acceptor). The formulation of this term is based on the condition that the hb interaction happens only when both the hb-donor and the hb-acceptor exist, and is always of opposite sign to the misfit energy, i.e., attractive, as the hb interaction's contribution is to decrease the total exchange energy:

$$E_{h-bond}(\sigma_m,\sigma_n) = C_{hb}\max[0,\sigma_{acc}-\sigma_{hb}]\min[0,\sigma_{don}+\sigma_{hb}],$$
$$\sigma_{hb} = 0.0084 \quad (11)$$

Sigma Profiles for Electrolytes

An important aspect of the extension of COSMO-SAC to electrolytes is the availability of sigma profiles. While a public sigma profile databank exists for molecular systems, there are no published sigma profile databanks available for electrolytes or ionic species. See Mullins, E., Oldland, R., Liu, Y. A., Wang, S., Sandler, S. I., Chen, C.-C., Zwolak, M., Seavey, K. C., Sigma-Profile Database for Using COSMO-Based Thermodynamic Methods, *Ind. Eng. Chem. Res.*, 2006, 45, 4389-4415. The electrolyte sigma profiles were generated by performing the quantum chemical COSMO calculations implemented in commercial package DMol3 (Accelrys, Inc., San Diego, Calif.). The procedure for obtaining the sigma profiles using DMol3 is described in Mullins, E., Oldland, R., Liu, Y. A., Wang, S., Sandler, S. I., Chen, C.-C., Zwolak, M., Seavey, K. C., Sigma-Profile Database for Using COSMO-Based Thermodynamic Methods, *Ind. Eng. Chem. Res.*, 2006, 45, 4389-4415. One electrolyte molecule (one anion atom and one cation atom) was first created with a desired separation distance between the anion charge center and the cation charge center. The sigma profile is then obtained by performing a single point energy COSMO solvation calculation with default settings. See Lin, S. T., Sandler, S. I., *A Priori* Phase Equilibrium Prediction from a Segment Contribution Solvation Model, *Ind. Eng. Chem. Res.*, 2002, 41, 899-913. Given the very limited availability of sigma profiles and the fact that elemental atomic radii for creating the COSMO molecular cavity are formally established only for 10 elements, NaCl, a 1-1 electrolyte, was used as a representative electrolyte. See Mullins, E., Oldland, R., Liu, Y. A., Wang, S., Sandler, S. I., Chen, C.-C., Zwolak, M., Seavey, K.

C., Sigma-Profile Database for Using COSMO-Based Thermodynamic Methods, *Ind. Eng. Chem. Res.*, 2006, 45, 4389-4415. The aim is to formulate a COSMO-SAC based activity coefficient model that provides a qualitative representation of the phase behavior of electrolyte systems. More electrolytes should be investigated and model parameters re-visited if and when sigma profiles become formally established for electrolytes. Furthermore, NaCl is considered to be completely dissociated in the liquid phase, a commonly used approximation that is valid only for strong electrolytes in dilute aqueous solutions. In addition, in the present invention, hydration of ions in aqueous solutions is not considered even though it is well known that hydration chemistry can have pronounced effects on electrolyte solution nonideality. See Chen, C.-C., Mathias, P. M., Orbey, H., Use of Hydration and Dissociation Chemistries with the Electrolyte NRTL Model, *AIChE J.*, 1999, 45, 1576-1586.

Instead of treating the sodium cation and the chloride anion as two distinct species and obtaining ionic sigma profiles individually, electrolyte sigma profiles are obtained herein that treat the cation and the anion as a pair, consistent with local electroneutrality, with a certain distance between the two ion charge centers. The Van der Waals radius of sodium cation is set to 2.27 Å, and that of chloride anion is set to 2.05 Å during the quantum calculation. While there are no obvious guidelines in setting the distance between the two ion centers, FIG. 1 shows sigma profiles of NaCl for four different charge center distances, between 2.7 Å and 4.0 Å. Electrolyte sigma profiles change with the charge center distance and they are not simple sums of sigma profiles of individual ions and counter-ions. With increasing distance, the width of the NaCl sigma profile increases slightly. When the distance is 2.7 Å, the range of the NaCl sigma profile is from −0.015 to 0.017 e/Å$^2$. When the distance increases to 4.0 Å, the sigma profile range is larger, from −0.016 to 0.019 e/Å$^2$. This is expected, because the longer the distance, the more polarized the surfaces of the cation and the anion become. Applicants use the sigma profile of NaCl with 2.7 Å distance as the base case. 2.7 Å is chosen because it is in line with the distance of the two ions in a crystal lattice (2.83 Å). See D. R. Lide (Ed.), *Handbook of Chemistry and Physics*, 77$^{th}$ Ed., CRC Press, 1996, p. 4-141. With different distances, the sigma profile of NaCl will be different, which affects the segment activity coefficients.

Extension of COSMO-SAC for Electrolytes

Short-range molecule-molecule, molecule-ion, and ion-ion interactions play the dominant role in determining the liquid phase nonideality of electrolyte solutions. See Chen, C.-C., Britt, H. I., Boston, J. F., Evans, L. B., Local Composition Model for Excess Gibbs Energy of Electrolyte Systems, Part I: Single Solvent, Single Completely Dissociated Electrolyte Systems, *AIChE J*, 1982, 28, 588-596. In the present invention's extension of the COSMO-SAC model to account for the short-range interaction contribution for electrolyte systems, it is recognized that the short-range interactions do not operate independently of the strong ion-ion electrostatic interactions. Thus, the extension takes into account two unique characteristics of electrolyte solution lattice structure resulting from the ion-ion interaction: 1) like-ion repulsion, and 2) local electroneutrality. Id. Like-ion repulsion states that, around a central cation or anion, there will be no ions of the same sign. Local electroneutrality states that the distribution of cations and anions around a central molecular species should satisfy electroneutrality. These two governing phenomena form the basis of the present invention's extension of COSMO-SAC for electrolyte systems including generation of sigma profiles for electrolytes.

COSMO-SAC, originally designed for neutral molecules, requires one sigma profile for each molecule as input information. In the present invention, Applicants use a dual sigma profile concept for electrolyte systems. The new concept treats surface segments of ionic species as distinct from surface segments of neutral molecules even if they are of the same surface charge. This distinction is justified on the basis that ionic sigma profiles carry net charges, i.e., positive for anions and negative for cations, while molecular sigma profiles carry no net charge. This dual sigma profile concept is essential in order to apply the like-ion repulsion and local electroneutrality hypotheses selectively to electrolyte systems.

In other words, instead of one sigma profile for each component, two sigma profiles are used to define one component. The first sigma profile represents surface segments from neutral molecules while the second sigma profile represents surface segments from ionic species that carry net charges. For instance, the water component carries two sigma profiles: the molecular sigma profile is constructed by the water molecule, and the ionic sigma profile is empty since there are no surface segments from charged species. For elemental electrolytes such as NaCl, the molecular sigma profile is empty since there are no segments from the neutral part, while the ionic sigma profile is constructed by the segments generated from the COSMO calculation for a pair of sodium cation and chloride anion. Certain species such as organic electrolytes may have both a non-empty molecular sigma profile and a non-empty ionic sigma profile. The sigma profile of each species, as obtained from DMol3, contains a listing of surface segments from neutral molecules and surface segments from cations or anions. FIGS. 2A-D show the dual sigma profiles for water, hexane and methanol solvents as well as the dual sigma profiles for the NaCl electrolyte.

The dual sigma profiles enable the examination of the three different types of short-range interaction: molecule-molecule, molecule-ion and ion-ion. The original COSMO-SAC formulation has been shown to provide an adequate account of the short-range molecule-molecule interaction and, to a certain extent, the short-range molecule-ion interaction. The local electroneutrality and like-ion repulsion hypotheses provide the conceptual basis to construct the sigma profile, to formulate the restoring free energy expressions for the ion-ion interaction, and to integrate the three types of short-range interaction: molecule-molecule, molecule-ion, and ion-ion.

The simplest case for electrolyte systems includes one molecular solvent and one elemental electrolyte. Here the solvent can be aqueous or non-aqueous. As mentioned previously, this application does not address partial dissociation of electrolytes, or hydration of ions, phenomena that are prevalent in electrolyte systems. Therefore, the model predictions are not expected to exactly match commonly reported "experimental" data on molal mean ionic activity coefficients or osmotic coefficients for electrolyte systems. Until partial dissociation and hydration of electrolytes are explicitly accounted for, such "experimental" data together with existing correlative activity coefficient models can only provide a reference to test whether the proposed model provides a qualitative representation of electrolyte systems.

Extended COSMO-SAC Term for the Short Range Interaction Contribution

In electrolyte systems with one molecular solvent and one elemental electrolyte, the solvent molecule, i.e., water, carries a molecular sigma profile while the elemental electrolyte, i.e., NaCl, carries an ionic sigma profile. The restoring free energy of the solute i in solution S is modified as below:

$$\frac{\Delta G^{*res}_{i/S}}{RT} = n_i \sum_{\substack{\sigma_m \in mole. \\ and\ ion}} p_i(\sigma_m) \ln \Gamma_S(\sigma_m) \quad (12)$$

$$\ln \Gamma_S(\sigma_m) = -\ln \left\{ \sum_{\substack{\sigma_m \in mole. \\ and\ ion}} p_S(\sigma_n) \Gamma_S(\sigma_n) \exp\left[\frac{-\Delta W(\sigma_m, \sigma_n)}{RT}\right] \right\} \quad (13)$$

The restoring free energy of the molecular solute i in its pure liquid is:

$$\frac{\Delta G^{*res}_{i/i}}{RT} = n_i \sum_{\sigma_m \in mole.} p_i(\sigma_m) \ln \Gamma_i(\sigma_m) \quad (14)$$

$$\ln \Gamma_i(\sigma_m) = -\ln \left\{ \sum_{\sigma_m \in mole.} p_i(\sigma_n) \Gamma_i(\sigma_n) \exp\left[\frac{-\Delta W(\sigma_m, \sigma_n)}{RT}\right] \right\} \quad (15)$$

The restoring free energy of the ionic solutes in pure electrolyte i is:

$$\frac{\Delta G^{*res}_{i/i}}{RT} = n_i \sum_{\sigma_m \in ion} p_i(\sigma_m) \ln \Gamma_i(\sigma_m) \quad (16)$$

$$\ln \Gamma_i(\sigma_m) = -\ln \left\{ \sum_{\sigma_m \in ion} p_i(\sigma_n) \Gamma_i(\sigma_n) \exp\left[\frac{-\Delta W(\sigma_m, \sigma_n)}{RT}\right] \right\} \quad (17)$$

Accordingly, the activity coefficient of species i can be modified as:

$$\ln \gamma^{COSMO-SAC}_{i/S} n_i \sum_{\substack{\sigma_m \in mole. \\ and\ ion}} p_i(\sigma_m) [\ln \Gamma_S(\sigma_m) - \ln \Gamma_i(\sigma_m)] \quad (18)$$

In Eqs. 12 and 13, "$\sigma_m \in$ mole. and ion" indicates surface segments from both the molecular sigma profile and the ionic sigma profile. The Staverman-Guggenheim combinatorial term is neglected in this application for model simplicity.

To account for the molecule-molecule interaction, the misfit exchange energy and the hydrogen bonding energy are retained as defined in COSMO-SAC for the exchange energy formulation for molecular sigma profiles.

$$\Delta W(\sigma_m, \sigma_n) = E_{misfit}(\sigma_m, \sigma_n) + E_{h\text{-}bond}(\sigma_m, \sigma_n) \quad (19)$$

where $\sigma_m$ and $\sigma_n$ are surface segments from the molecular sigma profile.

To account for the molecule-ion interaction, repulsion and attraction energy terms are introduced as:

$$\Delta W(\sigma_m, \sigma_n) = E_{repulsion}(\sigma_m, \sigma_n) + E_{attraction}(\sigma_m, \sigma_n) \quad (20)$$

where $\sigma_m$ and $\sigma_n$ are surface segments with one, $\sigma_m$, from the molecular sigma profile and the other, $\sigma_n$, from the ionic sigma profile. The specific forms of the repulsion energy term and the attraction energy term represent opportunities for model formulation. A general expression for the repulsion term can be:

$$E_{repulsion}(\sigma_m, \sigma_n) = C_1 \cdot (\sigma_m + \sigma_n)^2 \quad (21A)$$

In a specific embodiment, the repulsion term in Eq. 20 is set to be analogous to the misfit energy term with a factor $$E_{repulsion}(\sigma_m, \sigma_n) = C_1 \cdot \frac{f_{pol}\alpha}{2}(\sigma_m + \sigma_n)^2 \quad (21)$$

In a similar treatment, a general expression for the attraction term can be:

$$E_{attraction}(\sigma_m, \sigma_n) = C_2 \cdot \max[0, \sigma_+ - \sigma'] \min[0, \sigma_- + \sigma'], \quad (22A)$$

wherein $C_2$ is a factor, $\sigma_+$ is a surface segment with positive screening charge, $\sigma_-$ is a surface segment with negative screening charge, and $\sigma'$ is an adjustable parameter further specifying a minimum absolute value of $\sigma_+$ and $\sigma_-$ for a nonzero attraction energy. In a specific embodiment, the attraction term in Eq. 20 is set to be analogous to the hydrogen bonding energy term with a factor $C_2$:

$$E_{attraction}(\sigma_m, \sigma_n) = C_2 \cdot C_{hb} \max[0, \sigma_+ - \sigma_{cutoff}] \min[0, \sigma_- + \sigma_{cutoff}]. \quad (22)$$

The attraction term exists only if one of the two contacting surface segments carries a positive screening charge while the other carries a negative screening charge. The product of $C_2$ and $C_{hb}$ defines the slope of the attraction term and $\sigma_{cutoff}$ is an adjustable parameter further specifying a minimal absolute value in $\sigma_+$ and $\sigma_-$ before the attraction term is activated.

The ion-ion interaction formulation also contains repulsion and attraction terms:

$$\Delta W(\sigma_m, \sigma_n) = E'_{repulsion}(\sigma_m, \sigma_n) + E'_{attraction}(\sigma_m, \sigma_n) \quad (23)$$

where both $\sigma_m$ and $\sigma_n$ are surface segments from ionic sigma profiles. The repulsion term and the attraction term in Eq. 23 are set to be parallel to those of Eqs. 21-22 for the molecule-ion interaction with correction factors and cutoff charge density:

$$E'_{repulsion}(\sigma_m, \sigma_n) = C_3 \cdot \frac{f_{pol}\alpha}{2}(\sigma_m + \sigma_n)^2 \quad (24)$$

$$E'_{attraction}(\sigma_m, \sigma_n) = C_4 \cdot C_{hb} \max[0, \sigma_+ \sigma'_{cutoff}] \min[0, \sigma_- + \sigma'_{cutoff}] \quad (25)$$

Consistent with like-ion repulsion, the repulsion term should prevail for cation-cation interaction and anion-anion interaction while the attraction term should prevail for cation-anion interaction.

Eqs. 12-25 form the formulation of the extended COSMO-SAC term to calculate short range interactions for electrolyte systems. When electrolytes are removed from the system, there would be no ionic sigma profiles and the formulation reduces to the original COSMO-SAC model. The formulation is first tested below for single solvent-single electrolyte systems, and then further tested with multi electrolyte-single solvent and single electrolyte-multi solvent systems.

Extended Symmetric Pitzer-Debye-Hückel Term for the Long-Range Interaction Contribution The extended symmetric Pitzer-Debye-Hückel (PDH) model is used to account for the long-range ion-ion interactions. See Song, Y., Chen, C.-C., Symmetric Electrolyte Nonrandom Two-Liquid Activity Coefficient Model, *Ind. Eng. Chem. Res.*, 2009, 48, 7788-7797; Pitzer, K. S., Simonson, J.

M., Thermodynamics of Multicomponent, Miscible, Ionic Systems: Theory and Equations, *J. Phys. Chem.*, 1986, 90, 3005-3009. This symmetric model adopts the same pure solvent and pure electrolyte reference states as those of COSMO-SAC:

$$\frac{G^{ex,PDH}}{nRT} = -\frac{4A_\varphi I_x}{\rho} \ln\left[\frac{1+\rho I_x^{\frac{1}{2}}}{1+\rho (I_x^0)^{\frac{1}{2}}}\right] \quad (26)$$

with $$A_\varphi = \frac{1}{3}\left(\frac{2\pi N_A}{v_S}\right)^{\frac{1}{2}} \left(\frac{Q_e^2}{\varepsilon_S k_B T}\right)^{\frac{3}{2}} \quad (27)$$

$$I_x = \frac{1}{2}\sum_i z_i^2 x_i \quad (28)$$

where $G^{ex,PDH}$ is the excess Gibbs free energy due to the long-range ion-ion interactions, n is the total mole number of the solution, $A_\varphi$ is the Debye-Hückel parameter, $I_x$ is the ionic strength, $\rho$ is the closest approach parameter, $N_A$ is Avogadro's number, $v_S$ is the molar volume of the solvent, $Q_e$ is the electron charge, $\varepsilon_S$ is the dielectric constant of the solvent, $k_B$ is the Boltzmann constant, $z_i$ and $x_i$ are the charge number and mole fraction of component i, respectively, and $I_x^o$ represents $I_x$ at the symmetric reference state.

The PDH term for the long-range interaction contribution to the activity coefficient of component i has been summarized in the literature as being derived from Eq. 29. See Song, Y., Chen, C.-C., Symmetric Electrolyte Nonrandom Two-Liquid Activity Coefficient Model, *Ind. Eng. Chem. Res.*, 2009, 48, 7788-7797.

$$\ln \gamma_i^{PDH} = \frac{1}{RT}\left(\frac{\partial G^{ex,PDH}}{\partial n_i}\right)_{T,P,n_{j\neq i}} \quad i,j = \text{solvent, ion} \quad (29)$$

The final activity coefficient expression for the species, molecular or ionic, can be given as the sum of the short-range interaction contribution modeled by COSMO-SAC and the long-range interaction contribution determined by the PDH term:

$$\ln \gamma_i = \ln \gamma_i^{COSMO-SAC} + \ln \gamma_i^{PDH}, \quad i = \text{solvent, ion} \quad (30)$$

Exemplification

The eCOSMO-SAC formulation suggests up to six adjustable parameters: $C_1$, $C_2$, $\sigma_{cutoff}$ with the molecule-ion interaction contribution and $C_3$, $C_4$, $\sigma'_{cutoff}$ with the ion-ion interaction contribution. In the examples below, the same repulsion term and attraction term are assumed to apply to both molecule-ion interaction and ion-ion interaction. In other words, $C_1 = C_3$, $C_2 = C_4$, and $\sigma_{cutoff} = \sigma'_{cutoff}$. In addition, $\sigma_{cutoff}$ and $\sigma'_{cutoff}$ were also fixed at 0.0084 (e/Å$^2$), which is the same value as the cutoff for the hydrogen-bonding term in the original COSMO-SAC model for the molecule-molecule interaction. $C_1$ and $C_2$ are then adjusted to demonstrate and test the formulations of the present invention, eCOSMO-SAC.

NaCl with three different solvents, were investigated first. The activity coefficients of both solvents and ions were calculated with eCOSMO-SAC, and the results were compared with those calculated with eNRTL. The parameters used with the eNRTL model for the three electrolyte systems are obtained from the literature and shown in Table 1 below. See Chen, C.-C., Britt, H. I., Boston, J. F., Evans, L. B., Local Composition Model for Excess Gibbs Energy of Electrolyte Systems, Part I: Single Solvent, Single Completely Dissociated Electrolyte Systems, *AIChE J.*, 1982, 28, 588-596; Chen, C.-C., Song, Y., Extension of Non-Random Two-Liquid Segment Activity Coefficient Model for Electrolytes, *Ind. Eng. Chem. Res.*, 2005, 44, 8909-8921; Yang, S. O., Lee, C. S., Vapor-Liquid Equilibria of Water+Methanol in Presence of Mixed Salts, *J. Chem. Eng. Data*, 1998, 43, 558-561.

TABLE 1

Parameters used in the eNRTL model (Nonrandomness factor α = 0.2):

| Molecule (1) | Water | Hexane | Methanol |
|---|---|---|---|
| Electrolyte (2) | NaCl | NaCl | NaCl |
| $\tau_{12}$ | 8.885* | 15.000+ | 3.624# |
| $\tau_{21}$ | −4.549* | 5.000+ | −0.789# |

*regressed values from Chen et al. (1982)
+estimated values from Chen and Song (2005).
values from regression of experimental data of Yang and Lee (1998)

Elemental electrolytes are known to have limited solubilities in solvents, especially in nonaqueous solvents. The calculations and extrapolations with eNRTL provided an alternative to actual experimental data to examine the behavior of the eCOSMO-SAC formulation across the entire concentration range from pure solvents to pure electrolytes.

Three solvents were chosen in this application: water, hexane, and methanol. Water and hexane were chosen because they represent two distinctly different solvents: water being a hydrophilic solvent and hexane being a hydrophobic solvent. See Chen, C.-C., Song, Y., Extension of Non-Random Two-Liquid Segment Activity Coefficient Model for Electrolytes, *Ind. Eng. Chem. Res.*, 2005, 44, 8909-8921. Methanol was chosen as the third solvent because it represents a hybrid of hydrophilic solvent and hydrophobic solvent. Id. The new parameters $C_1$ and $C_2$ in the eCOSMO-SAC model were identified by matching the eCOSMO-SAC (present invention) predictions with the eNRTL calculation results for the NaCl-water binary. The eCOSMO-SAC predictions for the activity coefficients of the NaCl-hexane binary and the NaCl-methanol binary were then examined.

Figure 3:
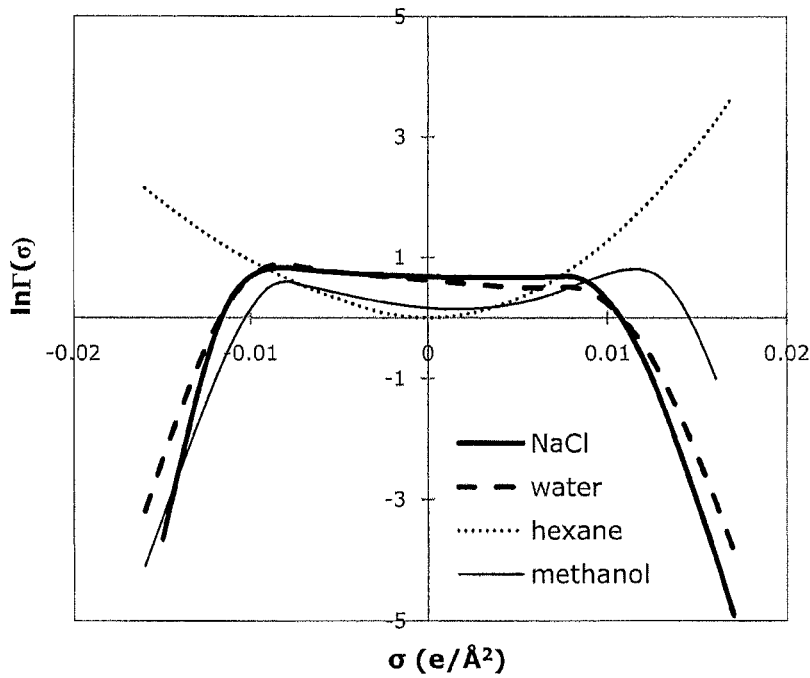
FIG. 3 is a graph of segment activity coefficients for electrolyte NaCl and solvents water, hexane and methanol.

FIG. 3 shows the segment activity coefficients for electrolyte NaCl and solvents water, hexane and methanol with $C_1$ and $C_2$ adjusted to 0.1 and 1.2, respectively. For solvents, the segment activity coefficients were the same as those from the original COSMO-SAC model. For electrolytes, the shape of the electrolyte segment activity coefficients would change with values for the new parameters. With the current cutoff values for ion-ion interaction and molecule-ion interaction set to be same as that for the hydrogen-bonding term, the shape of the electrolyte segment activity coefficient was similar to that of water.

Figure 4:
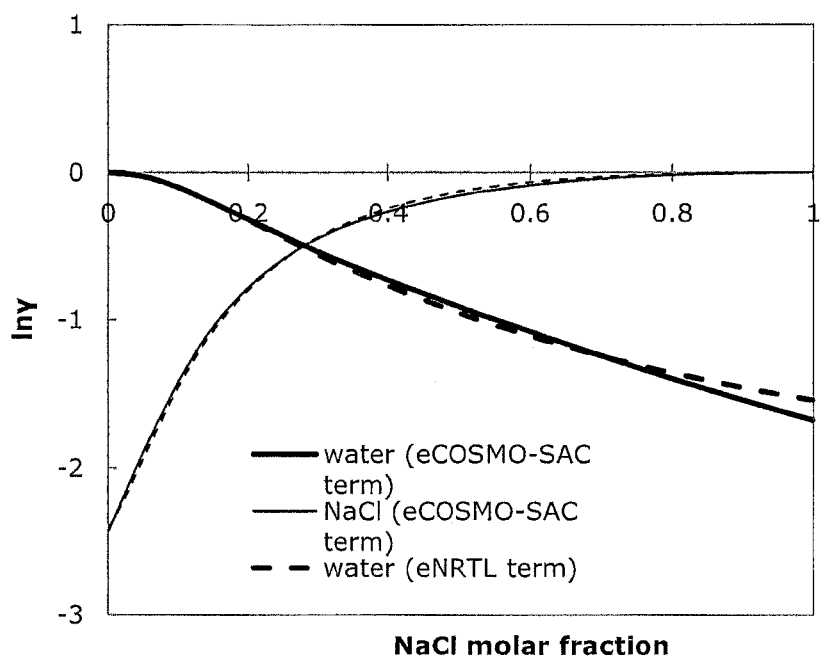
FIG. 4 is a graph of NaCl-water system activity coefficients calculated at 298.15 K with eCOSMO-SAC and eNRTL model (short-range term only).

The sigma profile of water distributed evenly over a wide region, suggesting that both the repulsion interaction and the attraction interaction are important. With $C_1$ and $C_2$ adjusted to 0.1 and 1.2, respectively, the mean ionic activity coefficients of NaCl and activity coefficients of water calculated by eCOSMO-SAC were found to closely match those calculated by eNRTL for NaCl-water binary across the entire concentration range. The eCOSMO-SAC (present invention) predictions and the eNRTL results are shown in FIG. 4. With an increase in NaCl molar fraction, the natural log of electrolyte activity coefficient as calculated by the short range term in eCOSMO-SAC or eNRTL increased from a negative value to zero for electrolyte NaCl and decreased from zero to a negative value for solvent water.

Figure 5:
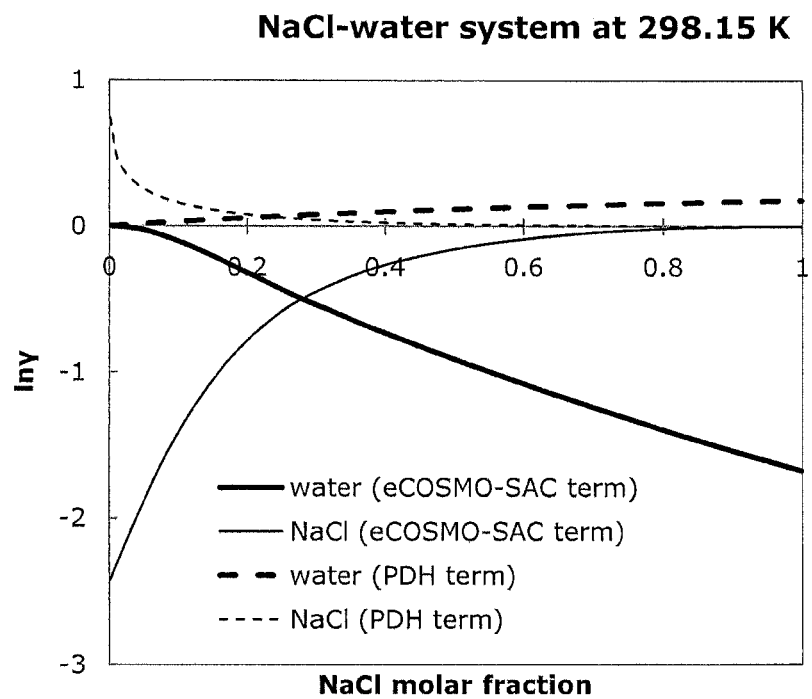
FIG. 5 is a graph of NaCl-water system activity coefficients calculated at 298.15 K with eCOSMO-SAC for both short-range term and long-range term contributions.
Figure 6:
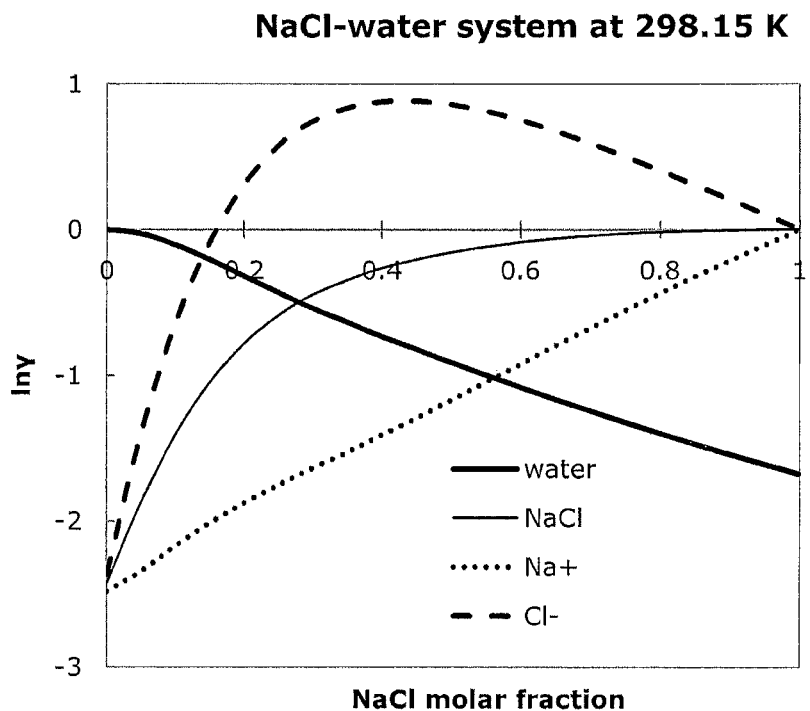
FIG. 6 is a graph of NaCl-water system ionic activity coefficients calculated at 298.15 K (short-range term only).

FIG. 5 shows the various contributions of activity coefficient calculations, i.e., the short-range eCOSMO-SAC term and the long-range PDH term. At dilute NaCl concentration, both the short-range eCOSMO-SAC term and the long-range PDH term had significant but opposite contributions to the electrolyte activity coefficient. At high NaCl concentration, the short-range eCOSMO-SAC term clearly dominated the water activity coefficient. FIG. 6 shows the eCOSMO-SAC short-range term contributions to activity coefficients for individual ionic species sodium cation and chloride anion. Following Eq. 18, they were calculated by summing the segment activity coefficient multiplied by sigma profile for each individual cation and anion. For the elemental electrolytes considered in this application, the positive surface segments of the ionic sigma profile were attributed to the anions and the negative surface segments were attributed to the cations.

For Na$^+$ cation, $$\ln\gamma_{i=Na^+/S}^{COSMO-SAC} = n_i \sum_{\sigma_m \in \text{cation}} p_i(\sigma_m)[\ln\Gamma_S(\sigma_m) - \ln\Gamma_i(\sigma_m)] \quad (31)$$

For Cl$^-$ anion, $$\ln\gamma_{i=Cl^-/S}^{COSMO-SAC} = n_i \sum_{\sigma_m \in \text{anion}} p_i(\sigma_m)[\ln\Gamma_S(\sigma_m) - \ln\Gamma_i(\sigma_m)] \quad (32)$$

For mean ionic activity coefficient of NaCl, $$\ln\gamma_{\pm,i/S}^{COSMO-SAC} = \frac{1}{2}\left(\ln\gamma_{i=Na^+/S}^{COSMO-SAC} + \ln\gamma_{i=Cl^-/S}^{COSMO-SAC}\right). \quad (33)$$

A general mean activity coefficient for each electrolyte can be represented by:

$$\ln\gamma_{\pm,i/S}^{COSMO-SAC} = \frac{1}{\nu}(\nu_c \ln\gamma_{i=cation/S}^{COSMO-SAC} + \nu_a \ln\gamma_{i=anion/S}^{COSMO-SAC}) \quad (34)$$

wherein $\gamma_{i=cation/S}^{COSMO-SAC}$ is the activity coefficient of each respective cation for the electrolyte, $\gamma_{i=anion/S}^{COSMO-SAC}$ is the activity coefficient of each respective anion for the electrolyte, $\nu_c$ is the cationic stoichiometric coefficient, $\nu_a$ is the anionic stoichiometric coefficient, and $\nu=\nu_c+\nu_a$. The ability to calculate individual ionic activity coefficients is considered as a significant advantage of the eCOSMO-SAC model of the present invention.

Figure 7:
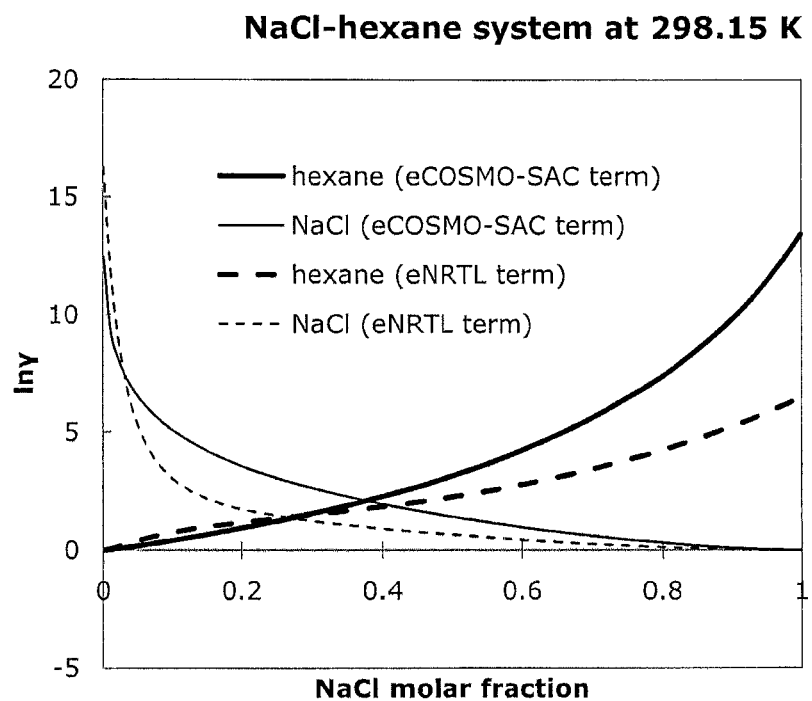
FIG. 7 is a graph of NaCl-hexane system activity coefficients calculated at 298.15 K with eCOSMO-SAC and eNRTL model (short-range term only).

As shown in FIGS. 2A-B, the molecular sigma profile of the hydrophobic solvent hexane is very simple. It is characterized by a high peak located near zero charge density, and no segment distribution in the high charge density region. The interaction between hydrophobic solvents and elemental electrolytes is known to be repulsive. Calculated with the same trial parameter set (i.e., $C_1=C_3=0.1$, $C_2=C_4=1.2$, $\sigma_{cutoff}=\sigma'_{cutoff}=0.0084$ (e/Å$^2$)), FIG. 7 shows the short range eCOSMO-SAC and eNRTL contributions to activity coefficients of sodium chloride electrolyte and solvent hexane. Only short-range contributions are shown in FIG. 7 because the two models share the same long-range PDH term. The trends and the orders of magnitude of activity coefficients of both solvent hexane and electrolyte NaCl calculated from eCOSMO-SAC were similar to those from eNRTL. With increasing NaCl molar fraction, the natural logarithm of activity coefficient decreased from a high positive value to zero for electrolyte NaCl and increased from zero to a high positive value for solvent hexane.

It is significant that, with the same parameter set, eCOSMO-SAC seems to be capable of describing phase behaviors of two opposite ends of electrolyte-solvent binary systems, i.e., NaCl in hydrophilic solvent water and NaCl in hydrophobic solvent hexane. Whether eCOSMO-SAC would qualitatively predict phase behavior of the NaCl-methanol binary was also examined. As mentioned earlier, methanol was chosen because the solvent is both hydrophilic (with the —OH group) and hydrophobic (with the —CH$_3$ group). The sigma profile of methanol, shown in FIG. 2, can be seen as a combination of the hexane sigma profile and the water sigma profile.

Figure 8:
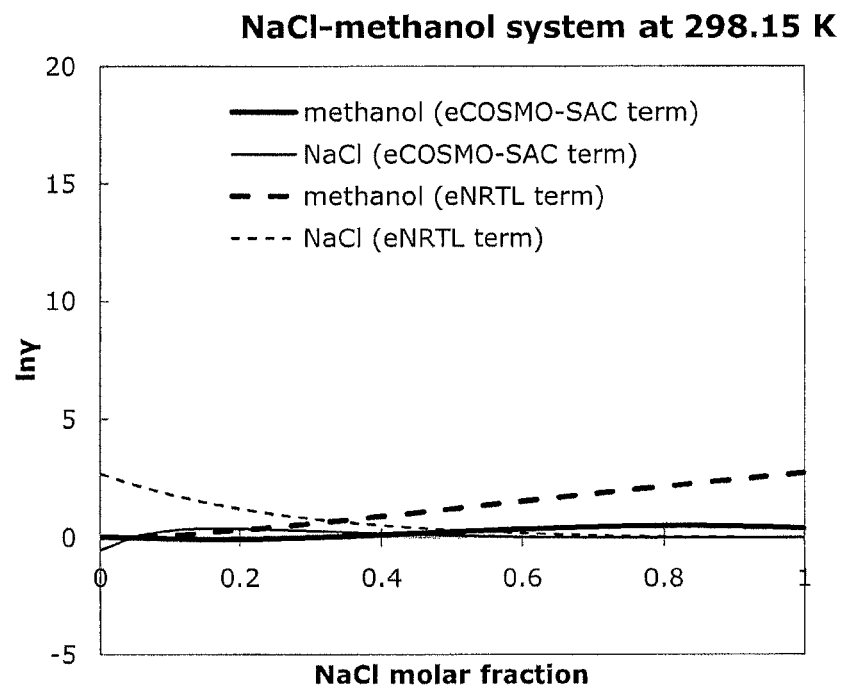
FIG. 8 is a graph of NaCl-methanol system activity coefficients calculated at 298.15 K with eCOSMO-SAC and eNRTL model (short-range term only).

FIG. 8 shows the activity coefficients of NaCl and methanol computed from eCOSMO-SAC and from eNRTL. Again, only the short-range term contributions are shown. The eCOSMO-SAC predictions for the NaCl-methanol binary represent interesting hybridization of those for the NaCl-water binary and the NaCl-hexane binary. While the eCOSMO-SAC predictions with the trial parameter set differ from those calculated by eNRTL, both eCOSMO-SAC and eNRTL yield relatively low positive values for the natural logarithm of the activity coefficients, predicting that methanol's infinite dilution activity coefficient should be higher than water's infinite dilution activity coefficient in the NaCl-solvent binary (FIG. 4) and lower than hexane's infinite dilution activity coefficient (FIG. 7), and predicting that the infinite dilution mean ionic activity coefficient in methanol should be higher than that in aqueous solution (FIG. 4) and lower than that in solvent hexane (FIG. 7).

Figure 9:
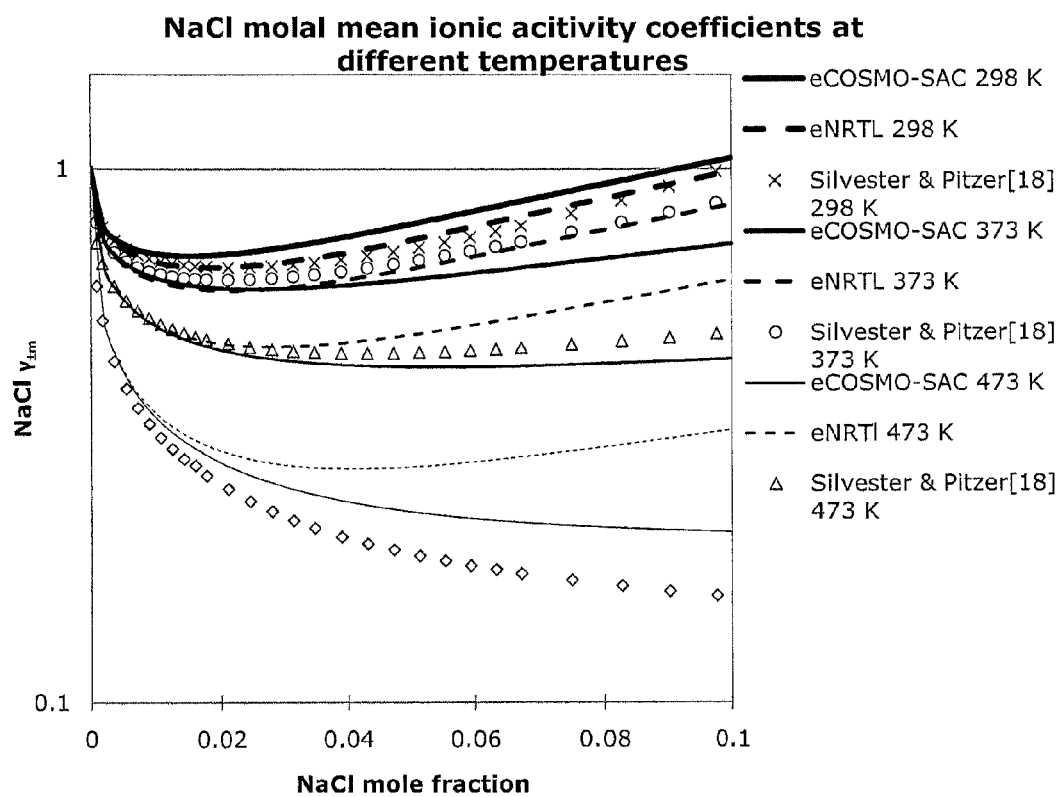
FIG. 9 is a graph of NaCl molal mean ionic activity coefficients at different temperatures with eCOSMO-SAC, eNRTL model and experimental data.
Figure 10A:
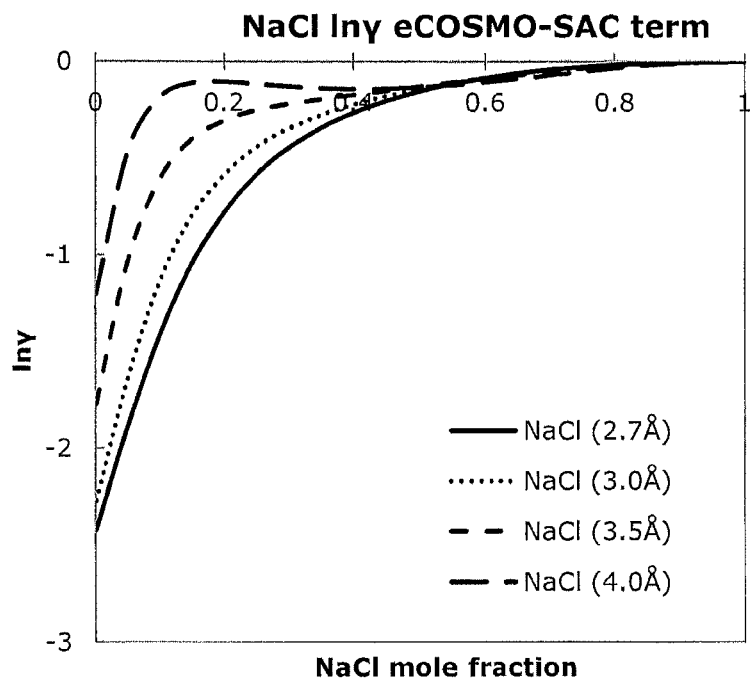
FIGS. 10A-F are graphs of effects of nuclei distance between cation and anion on three selected electrolyte systems at 298.15 K (short-range term only).
Figure 10B:
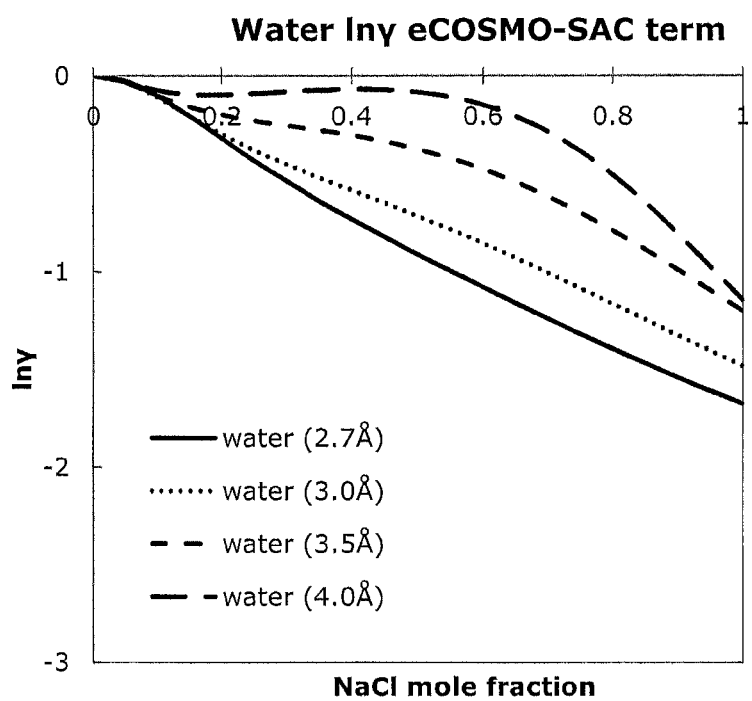
Figure 10C:
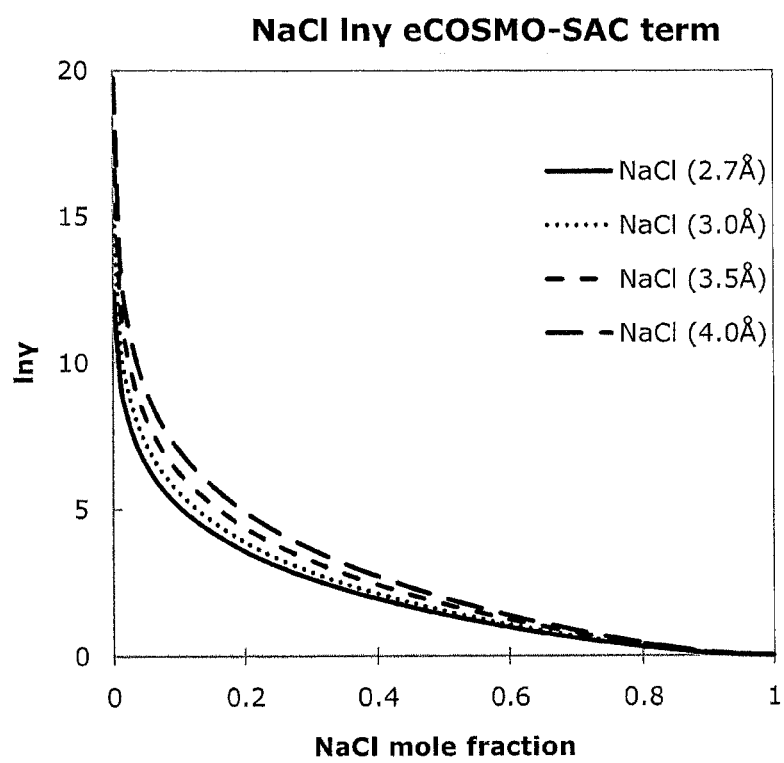
Figure 10D:
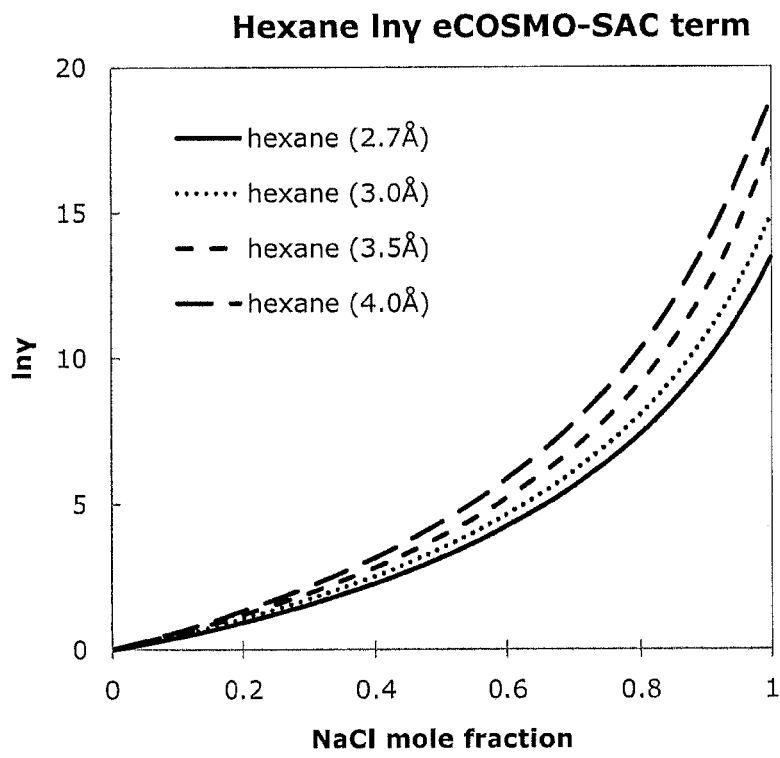
Figure 10E:
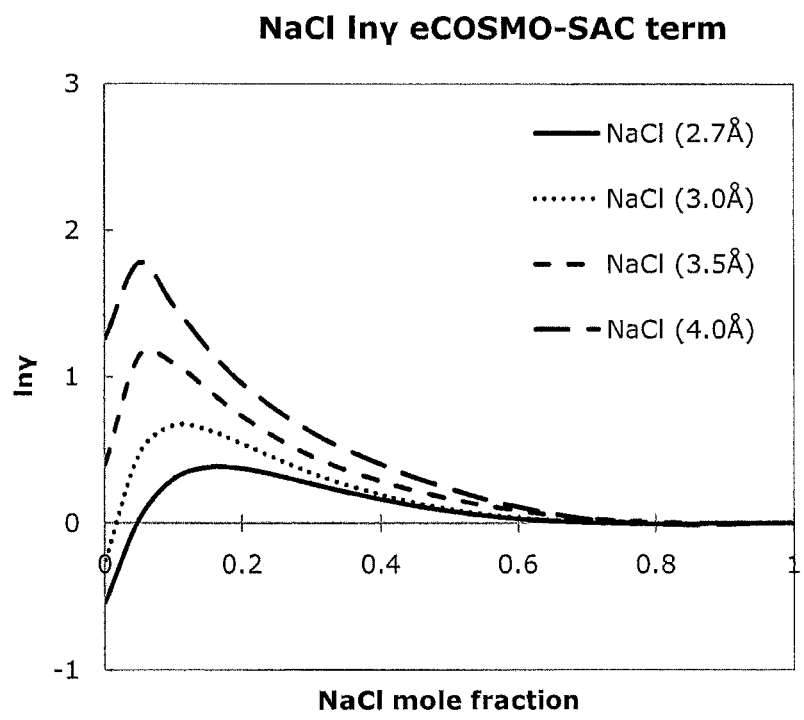
Figure 10F:
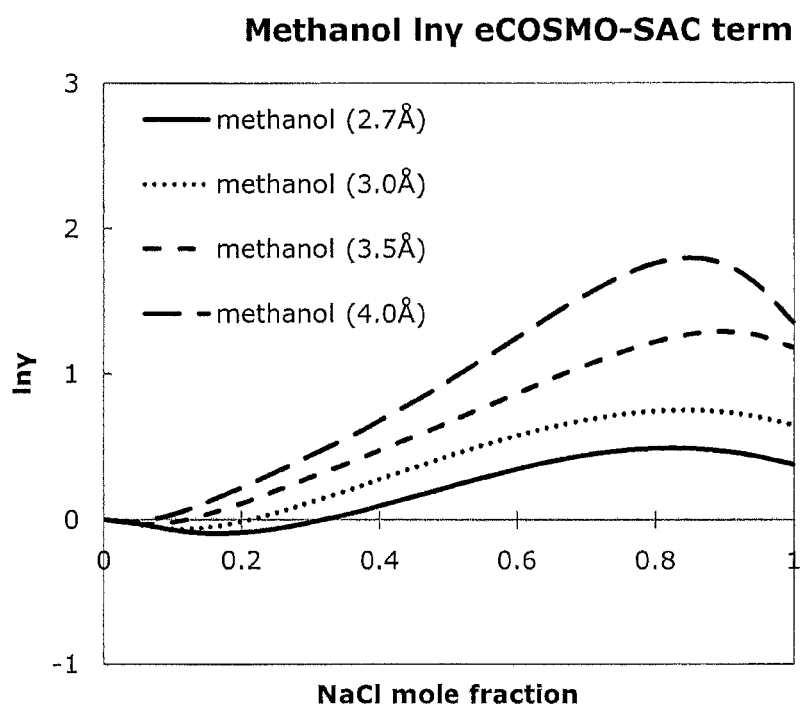
Figure 11A:
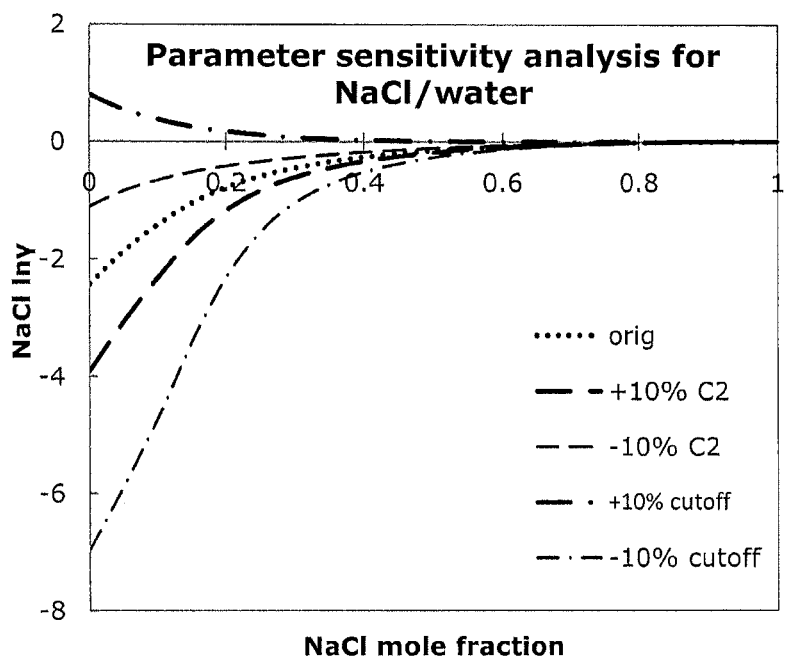
FIGS. 11A-D are graphs of parameter sensitivity analysis on NaCl-water and NaCl-hexane systems at 298.15 K (short-range term only).
Figure 11B:
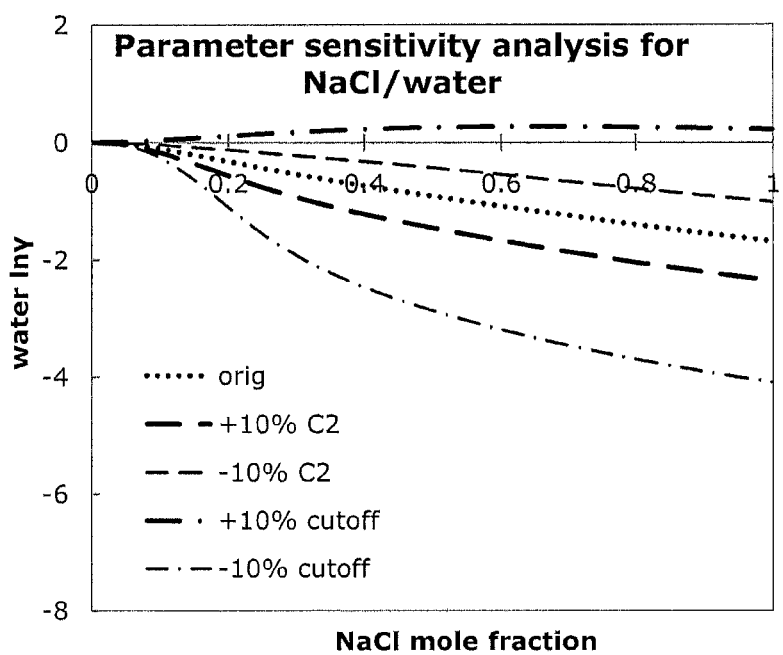
Figure 11C:
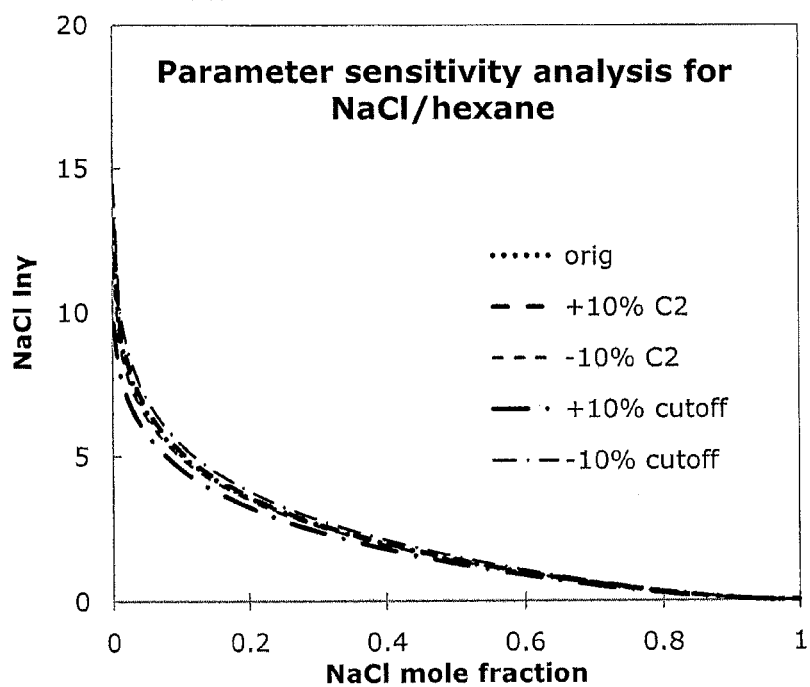
Figure 11D:
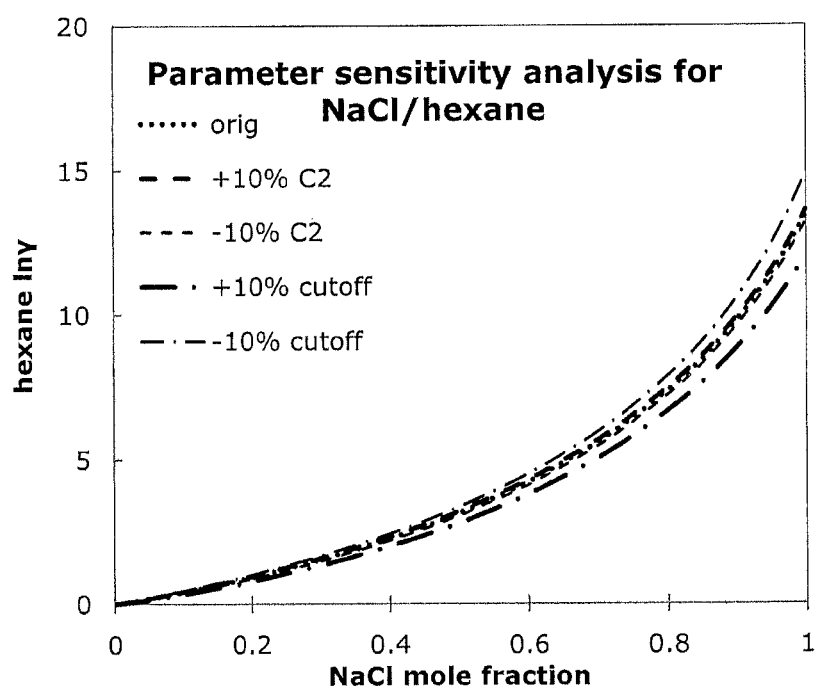

FIG. 9 shows the predicted molal mean ionic activity coefficients of aqueous NaCl from both eCOSMO-SAC model and eNRTL model. Also shown are the experimental data reported by Silvester & Pitzer at various temperatures. See Silvester, L. F., Pitzer, K. S. Thermodynamics of Geothermal Brines I. Thermodynamic Properties of Vapor-saturated NaCl (aq) Solutions from 0-300° C., Lawrence Berkeley Lab. Report LBL-4456, UC-66, TID-4500-R64, 1976, 23-25. With the model parameters set to be temperature-independent for both eCOSMO-SAC and eNRTL, the eCOSMO-SAC model gave better predictions than the eNRTL model does for molal mean ionic activity coefficients up to 573 K. It is interesting that the eCOSMO-SAC formulation of the present invention demonstrated promising predictive capability as it yielded the correct temperature trend across a wide temperature range.

Sensitivity Analysis

With the trial parameter set (i.e., $C_1=C_3=0.1$, $C_2=C_4=1.2$, $\sigma_{cutoff}=\sigma'_{cutoff}=0.0084$ (e/Å$^2$)), the eCOSMO-SAC formulation has shown promising potential as a predictive electrolyte thermodynamic model. The $C_1$ value of 0.1 suggested the original COSMO-SAC misfit energy term was too strong to account for the repulsion term for the molecule-ion and ion-ion interactions. On the other hand, the $C_2$ value of 1.2 suggested that the original COSMO-SAC hydrogen bonding energy term was probably in line with the attraction term for the molecule-ion and ion-ion interactions. To elucidate the sensitivities of the newly introduced parameters, the charge center distance effect on the activity coefficient calculations was first examined. A 10% perturbation to $C_1$ ($=C_3$), $C_2$ ($=C_4$) and $\sigma_{cutoff}$ ($=\sigma'_{cutoff}$) values was then introduced to illustrate model sensitivities to these parameters.

FIGS. 10A-F show the effect of charge center distance between sodium cation and chloride anion on the activity coefficient (ln γ) calculation for the three solvent-NaCl systems. With the increasing distance, the results of NaCl and solvent activity coefficients showed significant changes for the three systems. At dilute concentrations, ln γ of NaCl in NaCl-water changed from about −2.4 to about −1.2 and ln γ of water changed from about −1.6 to about −1.1 with distance increasing from 2.7 Å to 4.0 Å. ln γ of NaCl in NaCl-hexane changed from 12.4 to 19.7 and ln γ of hexane in NaCl-hexane changed from 13.4 to 18.8. ln γ of NaCl in NaCl-methanol changed from −0.5 to 1.3 and ln γ of methanol in NaCl-methanol changed from 0.4 to 1.4. The increase of the ln γ value for both electrolyte and solvents was expected, since larger distances between the cation and anion charge centers lead to more polarized sigma profiles. With the same values of parameters, the more polarized the sigma profiles became, the higher the values of activity coefficients were. The change of charge center distance had a similar impact for the three different electrolyte-solvent systems.

FIGS. 11A-D show the sensitivity analysis on the newly introduced parameters. Two systems, NaCl-water and NaCl-hexane, were examined. A perturbation of 10% of fitted parameter values was used to test the systems. The most sensitive parameter was $\sigma_{cutoff}(=\sigma'_{cutoff})$, followed by $C_2(=C_4)$, and $C_1(=C_3)$. Excluded from FIG. 11, the sensitivity on $C_1$ was very small due to its small parameter value. The cutoff value and $C_2$ had opposite impact on the results for both binary systems. Both increase in $\sigma_{cutoff}$ and decrease in $C_2$ led to weaker attractive interaction energy, while both decrease in $\sigma_{cutoff}$ and increase in $C_2$ led to stronger attractive interaction energy.

Figure 12:
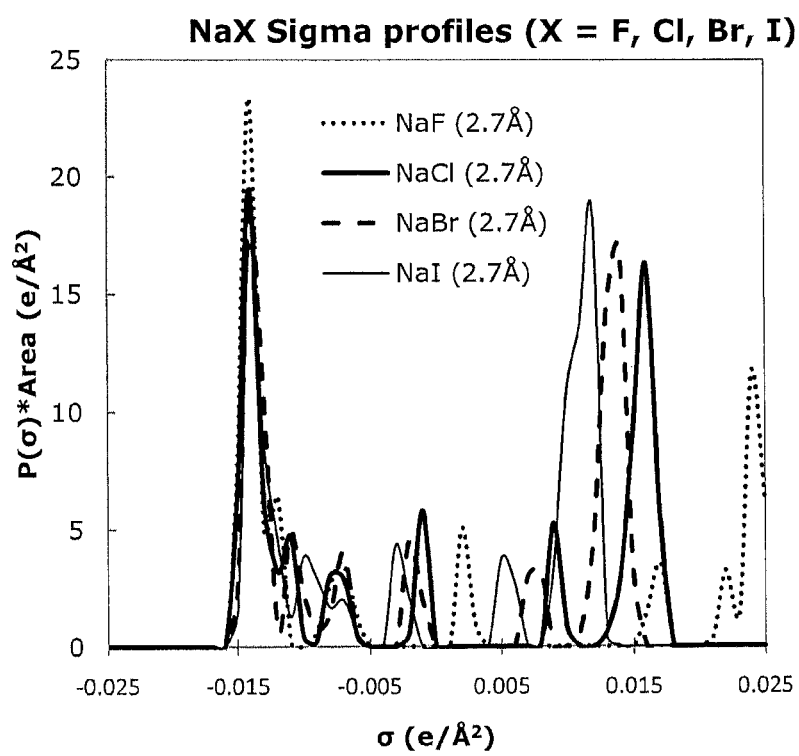
FIG. 12 is a graph of sigma profiles for NaCl, NaBr and NaI with nuclei distance 2.7 Å.

To illustrate the effect of ionic radius, FIG. 12 shows sigma profiles of NaF, NaBr and NaI compared with that of NaCl with the charge center distance fixed at 2.7 Å. The anion's radius varies from 1.72 Å for F, 2.05 Å for Cl, to 2.16 Å for Br, and 2.32 Å for I, resulting in the different shapes of sigma profiles shown in FIG. 12. Since the cation's radius is the same for the four electrolytes, the left sides of the sigma profiles exhibited trivial changes. With the increase in anion radius, the surface area of the anion increased and more segments had diluted charge density, leading to the peaks of the right side of the sigma profile shifting toward the center.

Figure 13A:
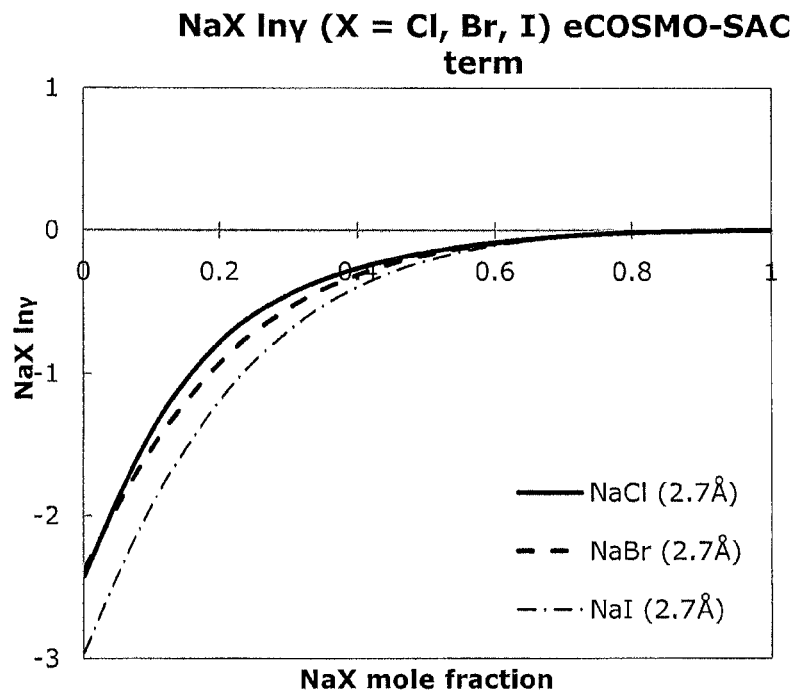
FIGS. 13A-B are graphs of NaX-water system activity coefficient calculations with nuclei distance 2.7 Å at 298.15 K; X=Cl, Br, I (short range term only).
Figure 13B:
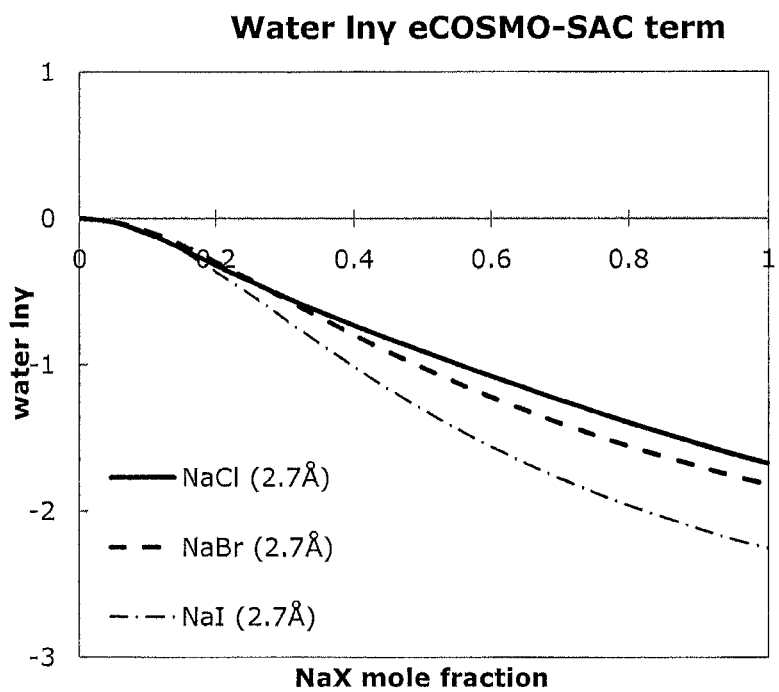

FIGS. 13A-B show the activity coefficient calculations for the three aqueous electrolyte systems. At the same composition, the activity coefficients for electrolyte and solvent decreased from NaCl to NaBr and NaI; the differences were more significant at dilute concentration, where the ln γ values changed from −2.4 to −3.0 for the electrolytes and −1.5 to −2.2 for solvent water. These results are consistent with the charge center distance effects shown in FIG. 10. More polarized sigma profiles (increasing distance) lead to increase in calculated ln γ while less polarized sigma profiles (increasing cation radii) lead to decrease in calculated ln γ.

Figure 14:
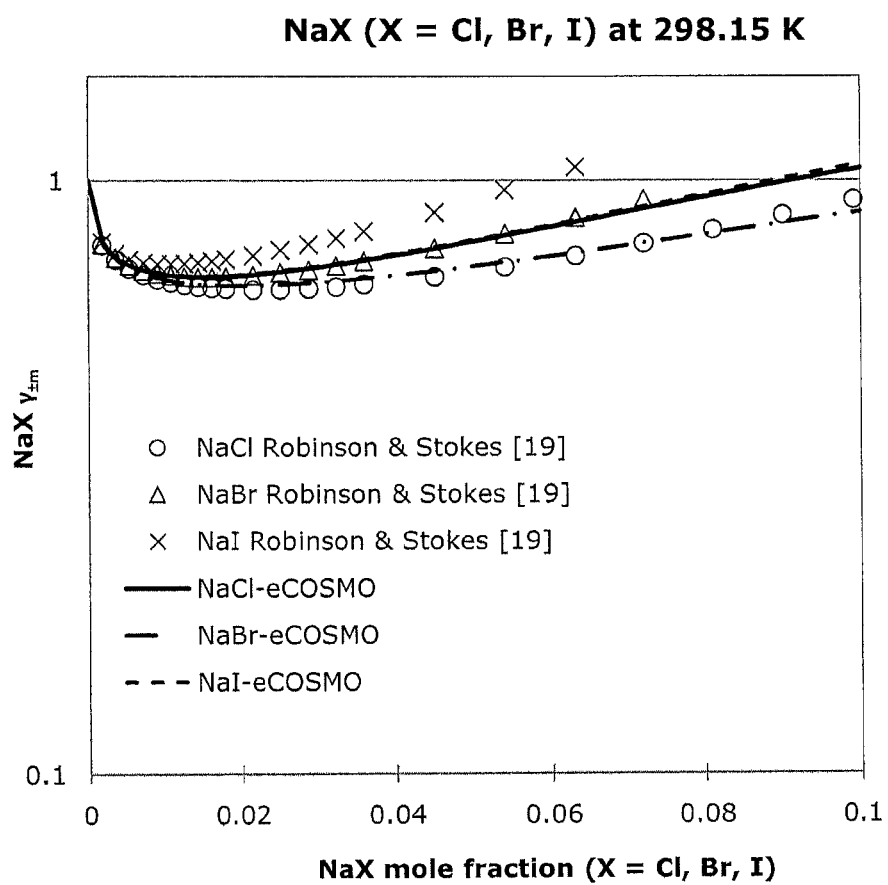
FIG. 14 is a graph of NaX molal mean ionic activity coefficients at 298.15 K with eCOSMO-SAC model and experimental data; X=Cl, Br, I.
Figure 15:
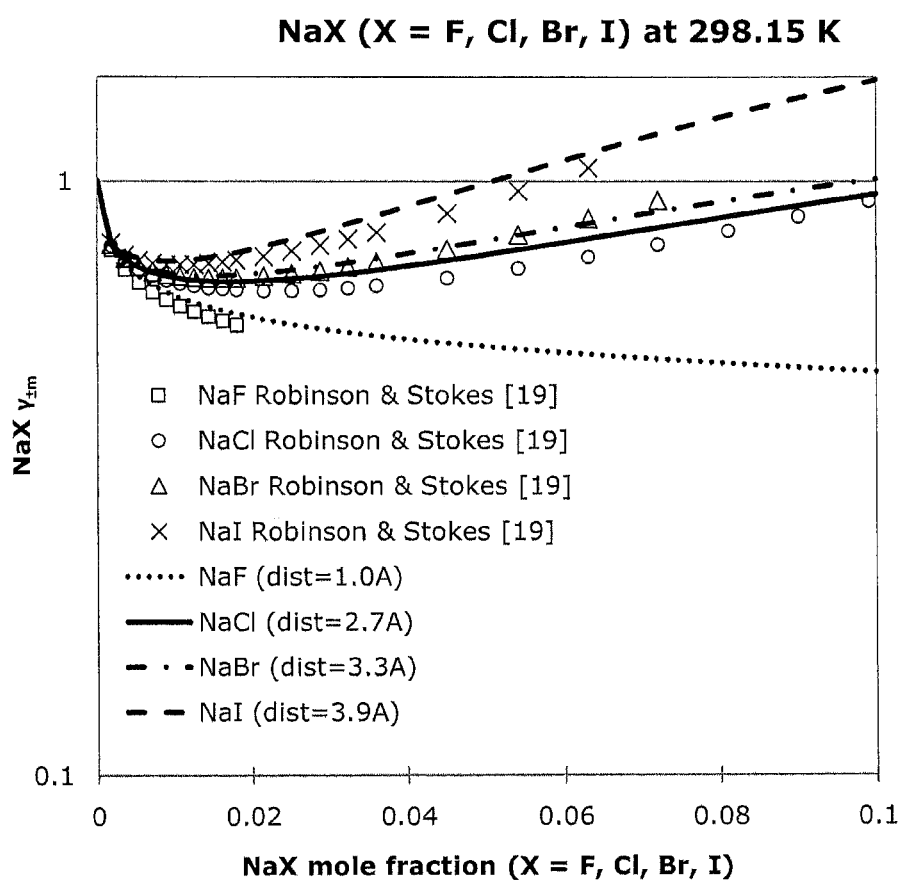
FIG. 15 is a graph of NaX molal mean ionic activity coefficients at 298.15 K with eCOSMO-SAC model and experimental data[19] using sigma profiles with adjusted charge center distance; X=F, Cl, Br, I.
Figure 16:
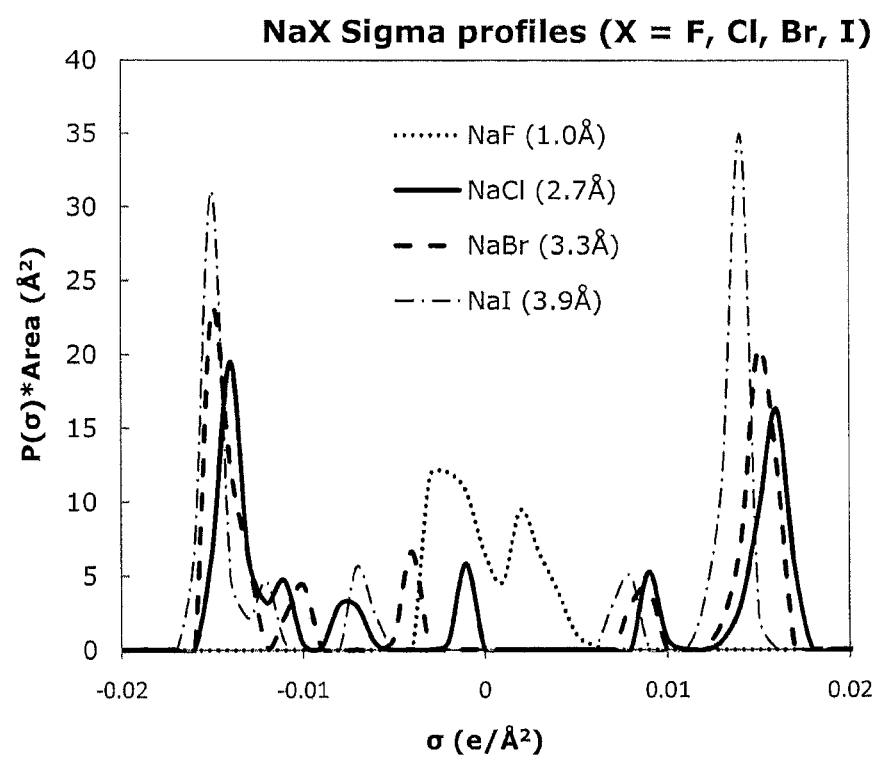
FIG. 16 is a graph of sigma profiles for NaF, NaCl, NaBr and NaI with charge center distance being 1.0 Å, 2.7 Å, 3.3 Å, and 3.9 Å, respectively.

Shown in FIG. 14 are the eCOSMO-SAC predictions and the experimental molal mean ionic activity coefficient ($\gamma_{\pm m}$) data of Robinson and Stokes for aqueous NaCl, NaBr and NaI at 298.15 K. See Robinson, R. A.; Stokes, R. H., Electrolyte Solutions, 2nd edition, Butterworths, London, 1959. The trial parameter set was used in the predictions, and the nuclei distances remained fixed at 2.7 Å. The eCOSMO-SAC predictions were qualitatively in line with the experimental data. However, the predictions did not yield the observed trend in molal mean ionic activity coefficients for the three electrolytes, i.e., $\gamma_{\pm m, NaI} > \gamma_{\pm m, NaBr} > \gamma_{\pm m, NaCl}$. This observed trend can be captured when the charge center distance is adjusted for each electrolyte, as shown in FIG. 15. Specifically, the $C_2$ (=$C_4$) parameter is first slightly changed from 1.2 to 1.18 Å to better match the experimental data for NaCl (with charge center distance fixed at 2.7 Å). The charge center distance is then adjusted for NaBr (3.3 Å) and NaI (3.9 Å) to match the data. The trend of charge center distance is in agreement with the data of crystal lattices for the electrolytes as NaI>NaBr>NaCl. Also shown in FIG. 15 are the experimental data and the model predictions (with charge center distance adjusted to 1 Å) for NaF. Note that these values (1.0 Å, 2.7 Å, 3.3 Å, 3.9 Å) used here for charge center distance are presented here only for illustration and can be modified along with other parameters as needed. FIG. 16 shows the corresponding electrolyte sigma profiles for NaF, NaCl, NaBr and NaI.

Figure 17:
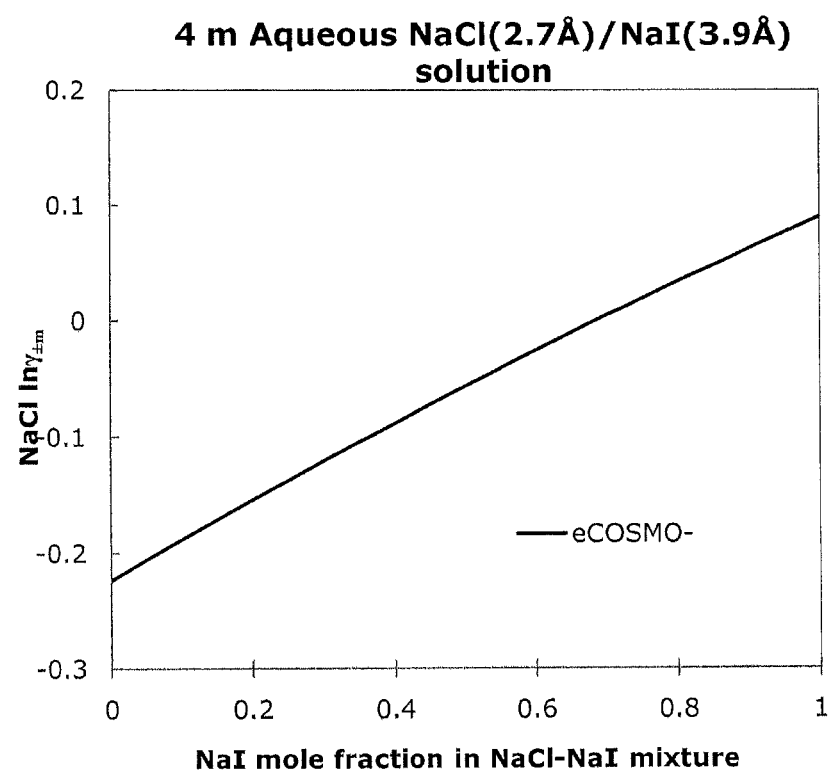
FIG. 17 is a graph of model predictions on NaCl molal mean ionic activity coefficient for a constant total molal (4 m) aqueous NaCl—NaI solution at 298.15 K.

For mixed electrolyte systems, Harned's rule should be followed, meaning that the logarithm of the molal mean ionic activity coefficient of one electrolyte in a mixture of constant molality is directly proportional to the molality of the other electrolytes. FIG. 17 shows the model predictions on NaCl molal mean ionic activity coefficient for an aqueous NaCl—NaI solution with a constant total electrolyte concentration of 4 m at 298.15 K. The results indicate the eCOSMO-SAC predictions are consistent with Harned's rule for mixed electrolyte systems.

Figure 18:
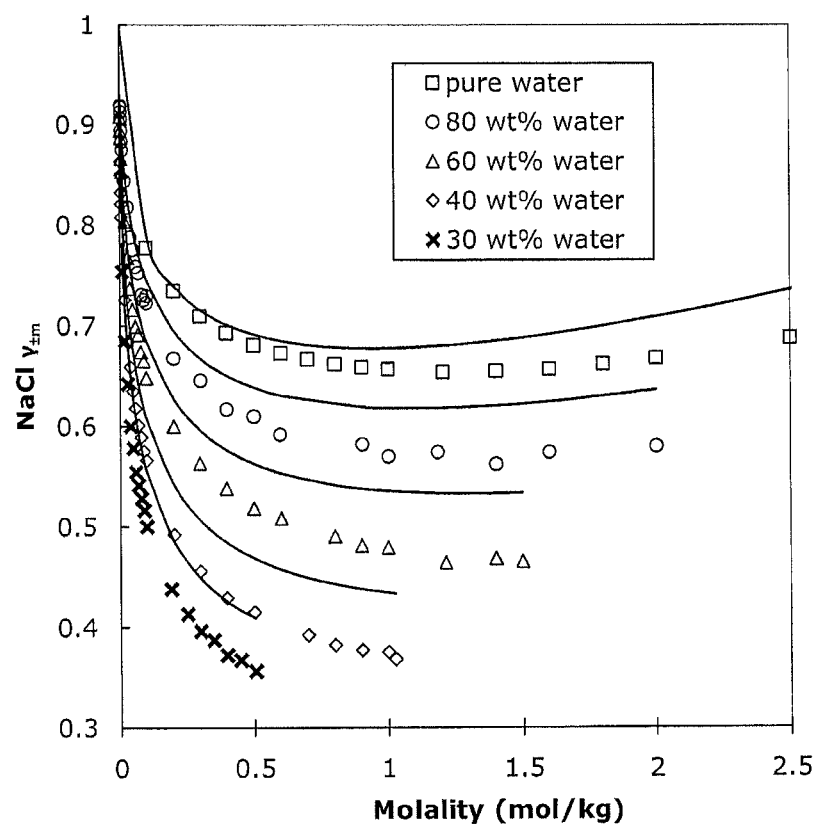
FIG. 18 is a graph of comparisons of model predictions (—) on NaCl molal mean ionic activity coefficient and the experimental data of Esteso et al. (1989) for NaCl in ethanol-water mixtures at 298.15 K.

FIG. 18 shows the comparison of the eCOSMO-SAC predictions on NaCl molal mean ionic activity coefficient and the experimental data of Esteso et al. for NaCl in ethanol-water mixtures at 298.15 K. See Esteso, M. A.; Gonzalez-Diaz, O. M.; Hernandez-Luis, F. F.; Fernandez-Merida, L., Activity Coefficients for NaCl in Ethanol-Water Mixtures at 25° C., *J. Solution Chem.*, 1989, 18, 277-288. The aqueous solution data shown in FIG. 18 are taken from Robinson and Stokes. See Robinson, R. A.; Stokes, R. H., Electrolyte Solutions, second edition, Butterworths, London, 1959. Note that here the mixed solvent infinite dilution reference state was used for the NaCl molal mean ionic activity coefficients. The model predictions, although slightly higher than the experimental data, clearly follow the qualitative trend of the experimental data as water wt % drops and ethanol wt % increases in the mixed solvent.

In a recently published article, Hsieh and Lin suggested an interesting and different approach to model electrolyte systems with COSMO-SAC. See Hsieh, M-T, Lin, S-T, A predictive model for the excess gibbs free energy of fully dissociated electrolyte solutions, *AIChE J.*, 2011, 57, 1061-1074. While the Hsieh and Lin model also applies the COSMO-SAC term for the short range interactions and a PDH term for the long range interactions, their model makes use of ion-specific sigma profiles. The model accounts for the short range interactions by introducing ten different types of surface segment interactions with twenty one different "sub-categories." It further introduces ten additional empirical equations containing eleven additional "universal" parameters to describe the interactions between ions and solvents. Furthermore, some of the elemental radii are treated as adjustable parameters to find optimal matches with experimental data on molal mean ionic activity coefficient. There are key differences between the Hsieh and Lin model and the model of this invention. In contrast to the Hsieh-Lin model that makes use of ion-specific sigma profiles, the model of this invention introduces a COSMO-SAC term that makes use of electrolyte sigma profiles. In addition, the model of this invention focuses on qualitative property trends for a few representative electrolyte systems while the Hsieh-Lin work correlated a comprehensive data set of molal mean ionic activity coefficients and osmotic coefficients for many electrolytes. Data on molal mean ionic activity coefficients and/or osmotic coefficients reflect the holistic effects of the short range interactions, the long range interactions, and others, including partial dissociation and hydration. With such electrolyte-specific experimental data, the aim of the model of this invention is to develop a predictive thermodynamic model based on electrolyte-specific sigma profiles.

Future model improvements should address general availability of sigma profiles for a wide variety of electrolytes, optimization of model parameters for a greater selection of electrolytes, model testing for mixed electrolytes, mixed solvents, as well as systems with ions of non-unary charges, and explicit account for the partial dissociation of electrolytes and hydration of ions.

CONCLUSIONS

An extension of COSMO-SAC is presented for electrolyte systems. The extension follows the like-ion repulsion and local electroneutrality hypotheses which govern the liquid lattice structure of electrolyte systems. In addition, a dual sigma profile concept is introduced for electrolytes to account for the short-range molecule-molecule, molecule-ion, and ion-ion interactions. The extension has been tested with three representative single-electrolyte, single-solvent systems and the results compared favorably to those calculated with the eNRTL model. Parameter sensitivity analysis performed on key model parameters and tests on selected systems showed that the model predictions were in qualitative agreement with experimental data. While extensive testing and further optimization are expected of the eCOSMO-SAC model, the encouraging results suggest that the proposed eCOSMO-SAC model formulation possesses the essential characteristics to evolve to a predictive electrolyte thermodynamic model.

Nomenclature $\ln \gamma_i^{COSMO\text{-}SAC}$=natural logarithm of activity coefficient of component i calculated from COSMO-SAC contribution $\ln \gamma_i^{PDH}$=natural logarithm of activity coefficient of component i calculated from symmetric Pitzer-Debye-Hückel contribution $\Delta G_{i/S}^{*res}$=restoring free energy of the solute i in solution S R=ideal gas constant; R=8.314 (kJ/kmol/K)

T=temperature (K)

$\sigma$=surface segment charge density (e/Å$^2$)

$n_i$=total number of segments for the component i $n_i(\sigma)$=number of segments that have charge density $\sigma$ $p_i(\sigma)$=sigma profile for component i $\Gamma_i(\sigma_m)$=segment activity coefficient for segment m of component i $\Sigma_{\sigma_m \in mole.}$=summation of all segments belonging to molecule $\Sigma_{\sigma_m \in cation}$=summation of all segments belonging to cation $\Sigma_{\sigma_m \in anion}$=summation of all segments belonging to anion $\Delta W(\sigma_m, \sigma_n)$=exchange energy between two segments with charge densities $\sigma_m$, $\sigma_n$ $E_{misfit}(\sigma_m, \sigma_n)$=misfit energy between two segments from molecule-molecule interaction with charge densities $\sigma_m$, $\sigma_n$ $E_{h\text{-}bond}(\sigma_m, \sigma_n)$=hydrogen bonding energy between two segments from molecule-molecule interaction with charge densities $\sigma_m$, $\sigma_n$ $f_{pol}\alpha/2$=the constant for the misfit energy; $f_{pol}\alpha/2$=8232.99 (Å$^4$×kcal/e$^2$/mol)

$C_{hb}$=the constant for the hydrogen bonding energy; $C_{hb}$=85580 (Å$^4$×kcal/e$^2$/mol)

$\sigma_{hb}$=the sigma cutoff value for hydrogen bonding; $\sigma_{hb}$=0.0084 (e/Å$^2$)

$E_{repulsion}(\sigma_m, \sigma_n)$=repulsion energy between two segments from molecule-ion interaction with charge densities $\sigma_m$, $\sigma_n$ (kcal/mol)

$E_{attraction}(\sigma_m, \sigma_n)$=attraction energy between two segments from molecule-ion interaction with charge densities $\sigma_m$, $\sigma_n$ (kcal/mol)

$E_{repulsion}'(\sigma_m, \sigma_n)$=repulsion energy between two segments from ion-ion interaction with charge densities $\sigma_m$, $\sigma_n$ (kcal/mol)

$E_{attraction}'(\sigma_m, \sigma_n)$=attraction energy between two segments from ion-ion interaction with charge densities $\sigma_m$, $\sigma_n$ (kcal/mol)

$C_1$, $C_3$=constant factor in the repulsion energy; $C_1=C_3=0.1$ $C_2$, $C_4$=constant factor in the attraction energy; $C_2=C_4=1.2$ $\sigma_{cutoff}$=the sigma cutoff value for attraction energy; $\sigma_{cutoff}$0.0084 (e/Å$^2$)

$\sigma_+$, $\sigma_-$=surface segments with positive charge and with negative charge (e/Å$^2$)

$A_\phi$=Debye-Hückel parameter $I_x$=ionic strength $\rho$=closest approach parameter; $\rho$=14.9

$N_A$=Avogadro's number; $N_A$=6.02251×10$^{23}$ (/mol)

$v_S$=molar volume of the solvent (cm$^3$/mol)

$Q_e$=electron charge; $Q_e$=4.80298×10$^{-10}$ (esu)

$\in_S$=dielectric constant of the solvent $k_B$=Boltzmann constant; $k_B$=1.38054×10$^{-16}$ (erg/K)

$z_i$=charge number of component i $x_i$=mole fraction of component i

The relevant teachings of all patents, published applications and references cited herein are incorporated by reference in their entirety.

Figure 19:
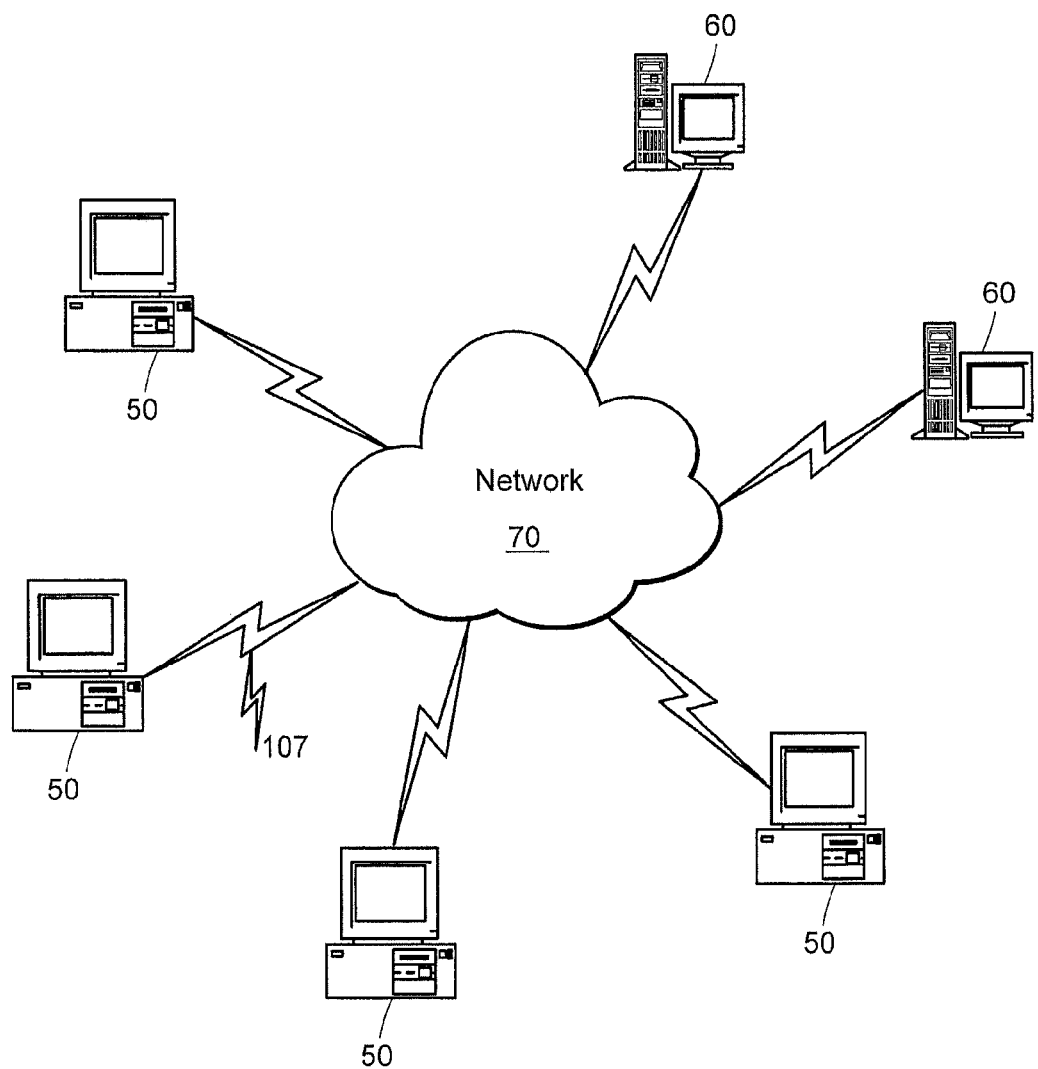
FIGS. 19 and 20 are schematic and block views, respectively, of a computer network embodiment of the present invention.

FIG. 19 illustrates a computer network or similar digital processing environment in which the present invention may be implemented.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 20:
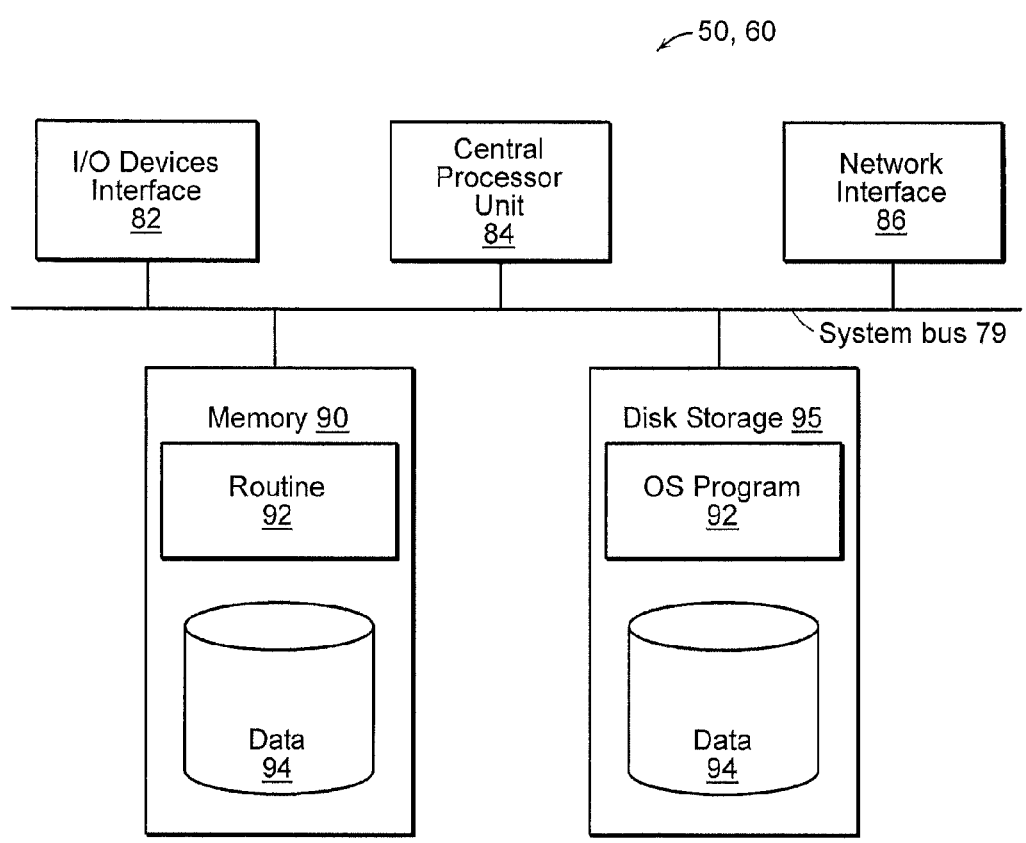

FIG. 20 is a diagram of the internal structure of a computer (e.g., client processor/device 50 or server computers 60) in the computer system of FIG. 19. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 19). Memory 90 provides volatile storage for computer software instructions 92 and data 94 used to implement an embodiment of the present invention (e.g., flowchart described below and shown in FIG. 21). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Figure 21:
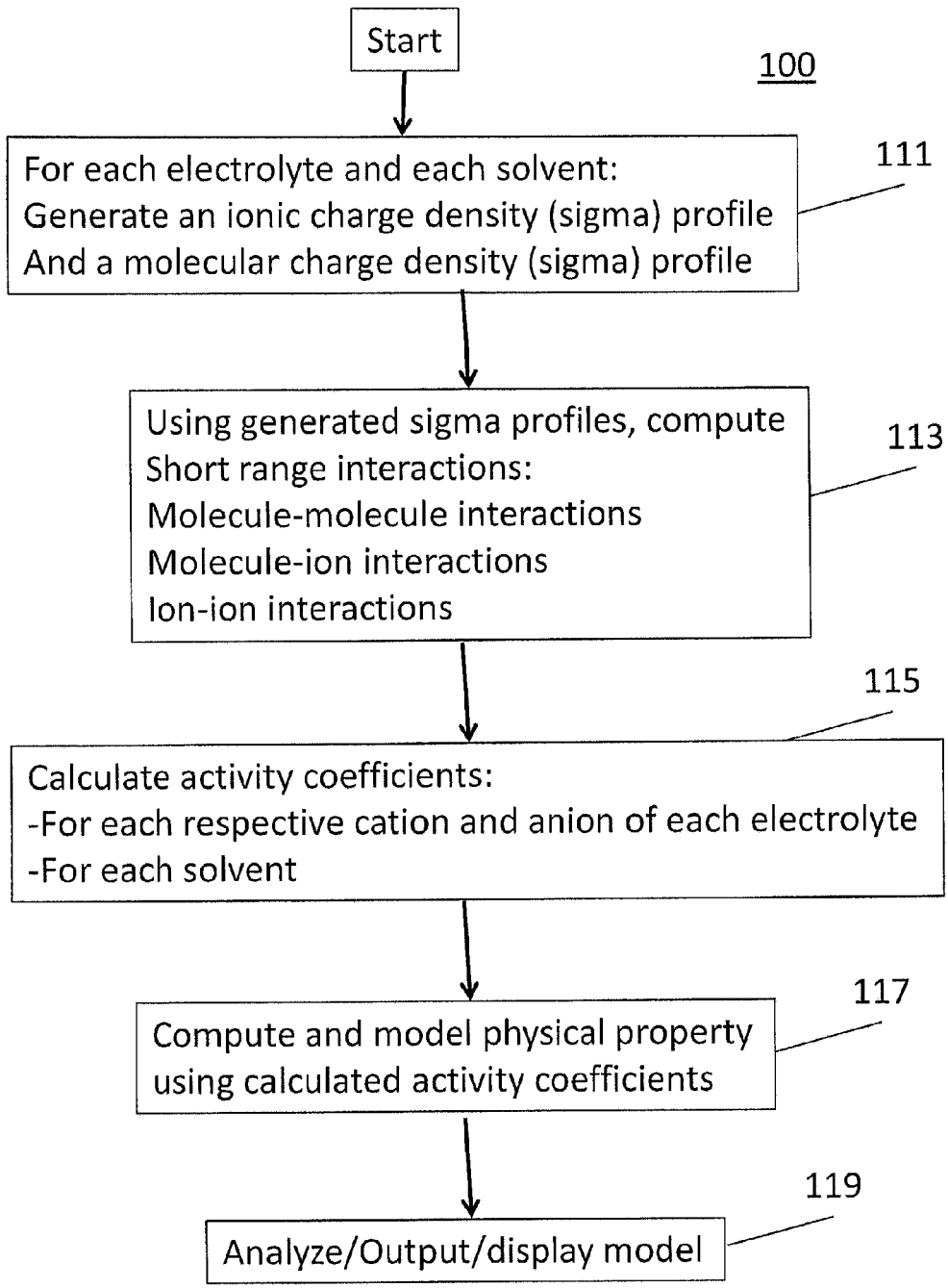
FIG. 21 is a flow diagram of one embodiment of the present invention.

In one embodiment, a method of modeling at least one physical property of a mixture of at least two chemical species that includes at least one electrolyte dissolved in one or more solvents using a modeler 100 is illustrated in FIG. 21. The modeling method (modeler 100) begins with or otherwise includes the computer implemented step 111 of generating an ionic charge density (sigma) profile and a molecular charge density (sigma) profile for each electrolyte and each solvent. The method further includes computing at step 113, using the generated sigma profiles, the short range interactions including: (i) calculating molecule-molecule interactions by using Eq. 19 and the molecular sigma profile of each electrolyte and each solvent, (ii) calculating molecule-ion interactions by using Eqs. 20-22 and the molecular sigma profile of each electrolyte and each solvent and the ionic sigma profile of each electrolyte and each solvent, and including repulsion (Eq. 21) and attraction (Eq. 22) energy terms, and (iii) calculating ion-ion interactions by using Eqs. 23-25 and the ionic sigma profiles of each electrolyte and each solvent, and including repulsion (Eq. 24) and attraction (Eq. 25) energy terms. The method then includes: (a) at step 115 calculating an activity coefficient for each respective cation and anion of each electrolyte and an activity coefficient for each solvent by combining in Eq. 30 a long-range interaction contribution with the computed short-range interaction contribution, and (b) using the calculated activity coefficients to compute at step 117 at least one physical property of the mixture. The computed physical property may include any one of vapor pressure, solubility, boiling point, freezing point, octanol/water partition coefficient, mean ionic activity coefficient (Eq. 33), osmotic coefficient, or a combination thereof.

Step 119 enables the computed physical property to be analyzed using the modeler 100. The analysis forms a model of the at least one physical property of the mixture, followed by the modeler 100 outputting the formed model to a computer display monitor. Generating the ionic and molecular sigma profiles for each electrolyte and each solvent includes computing a sigma profile for each electrolyte and each solvent, the sigma profile including charge density segments associated with charged atoms and charge density segments associated with neutral atoms.

While this invention has been particularly shown and described with references to example embodiments thereof, it will be understood by those skilled in the art that various changes in form and details may be made therein without departing from the scope of the invention encompassed by the appended claims.

What is claimed is:

1. A method of modeling at least one physical property of a mixture of at least two chemical species that includes at least one electrolyte dissolved in one or more solvents using a modeler, the method comprising the computer implemented steps of:
   a) generating an ionic charge density (sigma) profile and a molecular charge density (sigma) profile for each electrolyte and each solvent;
   b) using the generated sigma profiles, computing, using a computer, short range interactions including:
      i) calculating molecule-molecule interactions by using the molecular sigma profile of each electrolyte and each solvent;
      ii) calculating molecule-ion interactions by using the molecular sigma profile of each electrolyte and each solvent and the ionic sigma profile of each electrolyte and each solvent, and including repulsion and attraction energy terms; and
      iii) calculating ion-ion interactions by using the ionic sigma profiles of each electrolyte and each solvent, and including repulsion and attraction energy terms;
   c) calculating, using the computer, an activity coefficient for each respective cation and anion of each electrolyte and an activity coefficient for each solvent by combining a long-range interaction contribution with the computed short-range interaction contribution;
   d) using the calculated activity coefficients to compute, using the computer, at least one physical property of the mixture including any one of vapor pressure, solubility, boiling point, freezing point, octanol/water partition coefficient, mean ionic activity coefficient, osmotic coefficient, or a combination thereof;
   e) analyzing the computed physical property using the modeler, the analysis forming a model of the at least one physical property of the mixture; and
   f) outputting the formed model from the modeler to a computer display monitor.

2. The method of claim 1, wherein generating the ionic and molecular sigma profiles for each electrolyte and each solvent includes computing a sigma profile for each electrolyte and each solvent, the sigma profile including charge density segments associated with charged atoms and charge density segments associated with neutral atoms.

3. The method of claim 1, wherein calculating molecule-molecule interactions includes calculating:

$$\Delta W(\sigma_m,\sigma_n)=E_{misfit}(\sigma_m,\sigma_n)+E_{h\text{-}bond}(\sigma_m,\sigma_n),$$

$\Delta W(\sigma_m,\sigma_n)$=exchange energy between two segments with charge densities $\sigma_m$, $\sigma_n$ $E_{misfit}(\sigma_m,\sigma_n)$=misfit energy between two segments from molecule-molecule interaction with charge densities $\sigma_m$, $\sigma_n$ $E_{h\text{-}bond}(\sigma_m,\sigma_n)$=hydrogen bonding energy between two segments from molecule-molecule interaction with charge densities $\sigma_m$, $\sigma_n$.

4. The method of claim 1, wherein calculating molecule-ion interactions includes calculating:

$$\Delta W(\sigma_m,\sigma_n)=E_{repulsion}(\sigma_m,\sigma_n)+E_{attraction}(\sigma_m,\sigma_n),$$

$E_{repulsion}(\sigma_m,\sigma_n)$=repulsion energy between two segments from molecule-ion interaction with charge densities $\sigma_m$, $\sigma_n$ (kcal/mol)

$E_{attraction}(\sigma_m,\sigma_n)$=attraction energy between two segments from molecule-ion interaction with charge densities $\sigma_m$, $\sigma_n$ (kcal/mol).

5. The method of claim 4, wherein the repulsion energy term is represented by:

$$E_{repulsion}(\sigma_m,\sigma_n)=C_1 \cdot (\sigma_m+\sigma_n)^2,$$

$C_1$ is constant factor for the repulsion energy for molecule-ion interaction.

6. The method of claim 4, wherein the repulsion energy term is represented by:

$$E_{repulsion}(\sigma_m, \sigma_n) = C_1 \cdot \frac{f_{pol}\alpha}{2}(\sigma_m + \sigma_n)^2,$$

$f_{pol}\alpha/2$=the constant for the misfit energy $\frac{f_{pol}\alpha}{2}(\sigma_m + \sigma_n)^2$ is misfit energy.

7. The method of claim 4, wherein the attraction energy term is represented by:

$$E_{attraction}(\sigma_m,\sigma_n)=C_2 \cdot \max[0,\sigma_+ -\sigma']\min[0,\sigma_- +\sigma'],$$

$C_2$ is constant factor for the attraction energy for molecule-ion interaction, $\sigma_+$ is surface segment with positive screening charge, $\sigma_-$ is surface segment with negative screening charge, and $\sigma'$ is an adjustable parameter further specifying a minimum absolute value of $\sigma_+$ and $\sigma_-$ for a nonzero attraction energy.

8. The method of claim 4, wherein the attraction energy term is represented by:

$$E_{attraction}(\sigma_m,\sigma_n)=C_2 \cdot C_{hb}\max[0,\sigma_+ -\sigma_{cutoff}]\min[0,\sigma_- +\sigma_{cutoff}],$$

$C_{hb}\max[0,\sigma_+ -\sigma_{cutoff}]\min[0,\sigma_- +\sigma_{cutoff}]$ is hydrogen bonding energy, wherein $\sigma_+$ is surface segment with positive screening charge, $\sigma_-$ is surface segment with negative screening charge, $\sigma_{cutoff}$ is an adjustable parameter further specifying a minimum absolute value of $\sigma_+$ and $\sigma_-$ for a nonzero attraction energy.

9. The method of claim 1, wherein calculating ion-ion interactions includes calculating:

$$\Delta W(\sigma_m,\sigma_n)=E_{repulsion}'(\sigma_m,\sigma_n)+E_{attraction}'(\sigma_m,\sigma_n),$$

$E_{repulsion}'(\sigma_m,\sigma_n)$=repulsion energy between two segments from ion-ion interaction with charge densities $\sigma_m$, $\sigma_n$ (kcal/mol)

$E_{attraction}'(\sigma_m,\sigma_n)$=attraction energy between two segments from ion-ion interaction with charge densities $\sigma_m$, $\sigma_n$ (kcal/mol).

10. The method of claim 9, wherein the repulsion energy term is represented by:

$$E_{repulsion}'(\sigma_m,\sigma_n)=C_3 \cdot (\sigma_m+\sigma_n)^2,$$

$C_3$ is constant factor for the repulsion energy for ion-ion interaction.

11. The method of claim 9, wherein the repulsion energy term is represented by:

$$E_{repulsion}'(\sigma_m, \sigma_n) = C_3 \cdot \frac{f_{pol}\alpha}{2}(\sigma_m + \sigma_n)^2.$$

12. The method of claim 9, wherein the attraction energy term is represented by:

$$E_{attraction}'(\sigma_m,\sigma_n)=C_4 \cdot \max[0,\sigma_+ -\sigma']\min[0,\sigma_- +\sigma'],$$

$C_4$ is constant factor for the attraction energy for ion-ion interaction.

13. The method of claim 9, wherein the attraction energy term is represented by:

$$E_{attraction}'(\sigma_m,\sigma_n)=C_4 \cdot C_{hb}\max[0,\sigma_+ -\sigma'_{cutoff}]\min[0,\sigma_- +\sigma'_{cutoff}].$$

14. The method of claim 1, wherein calculating an activity coefficient for each respective cation and anion of each electrolyte and an activity coefficient for each solvent includes calculating:

$$\ln \gamma_i = \ln \gamma_i^{COSMO\text{-}SAC}+\ln \gamma_i^{PDH}, i=\text{solvent,ion}$$

wherein $\ln \gamma_i$ is natural logarithm of activity coefficient of component i, $\ln \gamma_i^{COSMO\text{-}SAC}$ is short range interaction contribution of each cation, anion, or solvent, and $\ln \gamma_i^{PDH}$ is long range interaction contribution.

15. The method of claim 14, wherein the activity coefficient for each respective cation of each electrolyte is represented by:

$$\ln \gamma_{i=cation/S}^{COSMO\text{-}SAC} = n_i \sum_{\sigma_m \in cation} p_i(\sigma_m)[\ln \Gamma_S(\sigma_m) - \ln \Gamma_i(\sigma_m)],$$

wherein $n_i$ is number of segments associated with cation i, $p_i(\sigma_m)$ is probability of a charge density $\sigma_m$ of the cation i, $\Gamma_S(\sigma_m)$ is activity coefficient for a segment with charge density $\sigma_m$ in solution S, and $\Gamma_i(\sigma_m)$ is activity coefficient for a segment with charge density $\sigma_m$ in cation i.

16. The method of claim 14, wherein the activity coefficient for each respective anion of each electrolyte is represented by:

$$\ln \gamma_{i=anion/S}^{COSMO-SAC} = n_i \sum_{\sigma_m \in anion} p_i(\sigma_m)[\ln \Gamma_S(\sigma_m) - \ln \Gamma_i(\sigma_m)],$$

wherein
$n_i$ is number of segments associated with anion i,
$p_i(\sigma_m)$ is probability of a charge density $\sigma_m$ of the anion i
$\Gamma_S(\sigma_m)$ is activity coefficient for a segment with charge density $\sigma_m$ in solution S, and
$\Gamma_i(\sigma_m)$ is activity coefficient for a segment with charge density $\sigma_m$ in anion i.

17. The method of claim 14, wherein the long range interaction contribution is represented by:

$$\ln \gamma_i^{PDH} = \frac{1}{RT}\left(\frac{\partial G^{ex,PDH}}{\partial n_i}\right)_{T,P,n_{j \neq i}} \quad i, j = \text{solvent, ion}$$

wherein
$\ln \gamma_i^{PDH}$ = natural logarithm of activity coefficient of component i calculated from symmetric Pitzer-Debye-Hückel contribution
R is gas constant,
T is temperature, and
$G^{ex,PDH}$ is excess Gibbs free energy due to tong range ion-ion interactions.

18. The method of claim 1, wherein mean activity coefficient for each electrolyte is represented by:

$$\ln \gamma_{\pm, i/S}^{COSMO-SAC} = \frac{1}{v}(v_c \ln \gamma_{i=cation/S}^{COSMO-SAC} + v_a \ln \gamma_{i=anion/S}^{COSMO-SAC}),$$

wherein
$\gamma_{i=cation/S}^{COSMO-SAC}$ is activity coefficient of each respective cation for the electrolyte,
$\gamma_{i=anion/S}^{COSMO-SAC}$ is activity coefficient of each respective anion for the electrolyte,
$v_c$ is cationic stoichiometric coefficient,
$v_a$ is anionic stoichiometric coefficient, and
$v = v_c + v_a$.

19. A computer apparatus for modeling at least one physical property of a mixture of at least two chemical species that includes at least one electrolyte dissolved in one or more solvents, comprising:
a digital processor member having an ionic charge density (sigma) profile and a molecular charge density (sigma) profile for each electrolyte and each solvent;
a processing unit operatively coupled to the digital processor member, the processing unit including a modeler modeling physical properties of mixtures, the processing unit:
(a) using the sigma profiles to compute short range interactions including:
i) calculating molecule-molecule interactions by using the molecular sigma profile of each electrolyte and the molecular sigma profile of each solvent;
ii) calculating molecule-ion interactions by using the molecular sigma profile of each electrolyte and each solvent and the ionic sigma profile of each electrolyte and each solvent, and including repulsion and attraction energy terms; and
iii) calculating ion-ion interactions by using the ionic sigma profiles of each electrolyte and each solvent, and including repulsion and attraction energy terms;
(b) calculating an activity coefficient for each respective cation and anion of each electrolyte and an activity coefficient for each solvent by combining a long-range interaction contribution with the computed short-range interaction contribution;
(c) using the calculated activity coefficients to compute at least one physical property of the mixture including any one of vapor pressure, solubility, boiling point, freezing point, octanol/water partition coefficient, mean ionic activity coefficient, osmotic coefficient, or a combination thereof; and
(d) analyzing the computed physical property using the modeler, the analysis forming a model of the at least one physical property of the mixture; and
an output module coupled to receive the formed model and to provide an indication of the formed model as output.

20. The computer apparatus of claim 19, wherein the ionic and molecular sigma profiles for each electrolyte and each solvent are generated by computing a sigma profile for each electrolyte and each solvent, the sigma profile including charge density segments associated with charged atoms and charge density segments associated with neutral atoms.

21. The computer apparatus of claim 19, wherein the processing unit calculating molecule-molecule interactions includes calculating:

$$\Delta W(\sigma_m, \sigma_n) = E_{misfit}(\sigma_m, \sigma_n) + E_{h-bond}(\sigma_m, \sigma_n),$$

$\Delta W(\sigma_m, \sigma_n)$ exchange energy between two segments h charge densities $\sigma_m$, $\sigma_n$
$E_{misfit}(\sigma_m, \sigma_n)$ = misfit energy between two segments from molecule-molecule interaction with charge densities $\sigma_m$, $\sigma_n$
$E_{h-bond}(\sigma_m, \sigma_n)$ = hydrogen bonding energy between two segments from molecule-molecule interaction with charge densities $\sigma_m$, $\sigma_n$.

22. The computer apparatus of claim 19, wherein the processing unit calculating molecule-ion interactions includes calculating:

$$\Delta W(\sigma_m, \sigma_n) = E_{repulsion}(\sigma_m, \sigma_n) + E_{attraction}(\sigma_m, \sigma_n),$$

$E_{repulsion}(\sigma_m, \sigma_n)$ = repulsion energy between two segments from molecule-ion interaction with charge densities $\sigma_m$, $\sigma_n$ (kcal/mol)
$E_{attraction}(\sigma_m, \sigma_n)$ = attraction energy between two segments from molecule-ion interaction with charge densities $\sigma_m$, $\sigma_n$ (kcal/mol)

$$\Delta W(\sigma_m, \sigma_n) = E_{repulsion}(\sigma_m, \sigma_n) + E_{attraction}(\sigma_m, \sigma_n),$$

wherein
$\Delta W$ is exchange energy,
$E_{repulsion}(\sigma_m, \sigma_n)$ is repulsion energy,
$E_{attraction}(\sigma_m, \sigma_n)$ is attraction energy,
$\sigma_m$ is surface segment from molecular sigma profile, and
$\sigma_n$ is surface segment from ionic sigma profile.

23. The computer apparatus of claim 22, wherein the repulsion energy term is represented by:

$$E_{repulsion}(\sigma_m,\sigma_n) = C_1 \cdot (\sigma_m + \sigma_n)^2,$$

$C_1$ is constant factor for the repulsion energy.

24. The computer apparatus of claim 22, wherein the repulsion energy term is represented by:

$$E_{repulsion}(\sigma_m, \sigma_n) = C_1 \cdot \frac{f_{pol}\alpha}{2}(\sigma_m + \sigma_n)^2,$$

$f_{pol}\alpha/2$=the constant for the misfit energy $\frac{f_{pol}\alpha}{2}(\sigma_m + \sigma_n)^2$ is misfit energy.

25. The computer apparatus of claim 22, wherein the attraction energy term is represented by:

$$E_{attraction}(\sigma_m,\sigma_n) = C_2 \cdot \max[0,\sigma_+ -\sigma']\min[0,\sigma_- +\sigma'],$$

$C_2$ is constant factor for the attraction energy,
  $\sigma_+$ is surface segment with positive screening charge,
  $\sigma_-$ is surface segment with negative screening charge, and
  $\sigma'$ is an adjustable parameter further specifying a minimum, absolute value of $\sigma_+$ and $\sigma_-$ for a nonzero attraction energy.

26. The computer apparatus of claim 22, wherein the attraction energy term is represented by:

$$E_{attraction}(\sigma_m,\sigma_n) = C_2 \cdot C_{hb}\max[0,\sigma_+ -\sigma_{cutoff}]\min[0,\sigma_- +\sigma_{cutoff}],$$

$C_{hb}\max[0,\sigma_+ -\sigma_{cutoff}]\min[0,\sigma_- +\sigma_{cutoff}]$ is hydrogen bonding energy, wherein
  $\sigma_+$ is surface segment with positive screening charge,
  $\sigma_-$ is surface segment with negative screening charge,
  $\sigma_{cutoff}$ is an adjustable parameter further specifying a minimum absolute value of $\sigma_+$ and $\sigma_-$ for a nonzero attraction energy.

27. The computer apparatus of claim 19, wherein the processing unit calculating ion-ion interactions includes calculating:
calculating:

$$\Delta W(\sigma_m,\sigma_n) = E_{repulsion}'(\sigma_m,\sigma_n) + E_{attraction}'(\sigma_m,\sigma_n),$$

$E_{repulsion}'(\sigma_m,\sigma_n)$=repulsion energy between two segments from ion-ion interaction with charge densities $\sigma_m$, $\sigma_n$ (kcal/mol)
$E_{attraction}'(\sigma_m,\sigma_n)$=attraction energy between two segments from ion-ion interaction with charge densities $\sigma_m$, $\sigma_n$ (kcal/mol).

28. The computer apparatus of claim 27, wherein the repulsion energy term is represented by:

$$E_{repulsion}'(\sigma_m,\sigma_n) = C_3 \cdot (\sigma_m + \sigma_n)^2,$$

$C_3$ is constant factor for the repulsion energy for ion-ion interaction.

29. The computer apparatus of claim 27, wherein the repulsion energy term is represented by:

$$E_{repulsion}'(\sigma_m, \sigma_n) = C_3 \cdot \frac{f_{pol}\alpha}{2}(\sigma_m + \sigma_n)^2.$$

30. The computer apparatus of claim 27, wherein the attraction energy term is represented by:

$$E_{attraction}'(\sigma_m,\sigma_n) = C_4 \cdot \max[0,\sigma_+ -\sigma']\min[0,\sigma_- +\sigma'],$$

$C_4$ is constant factor for the attraction energy for ion-ion interaction.

31. The computer apparatus of claim 27, wherein the attraction energy term is represented by:

$$E_{attraction}'(\sigma_m,\sigma_n) = C_4 \cdot C_{hb}\max[0,\sigma_+ -\sigma'_{cutoff}]\min[0,\sigma_- +\sigma'_{cutoff}].$$

32. The computer apparatus of claim 19, wherein the processing unit calculating an activity coefficient for each respective cation and anion of each electrolyte and an activity coefficient for each solvent includes calculating:

$$\ln \gamma_i = \ln \gamma_i^{COSMO\text{-}SAC} + \ln \gamma_i^{PDH}, \; i=\text{solvent,ion}$$

wherein
  $\ln \gamma_i$ is natural logarithm of activity coefficient of component i,
  $\ln \gamma_i^{COSMO\text{-}SAC}$ is short range interaction contribution of each cation, anion, or solvent, and
  $\ln \gamma_i^{PDH}$ is long range interaction contribution.

33. The computer apparatus of claim 32, wherein the activity coefficient for each respective cation of each electrolyte is represented by:

$$\ln \gamma_{i=cation/S}^{COSMO\text{-}SAC} = n_i \sum_{\sigma_m \in cation} p_i(\sigma_m)[\ln \Gamma_S(\sigma_m) - \ln \Gamma_i(\sigma_m)],$$

wherein
  $n_i$ is number of segments associated with cation i,
  $p_i(\sigma_m)$ is probability of a charge density $\sigma_m$ of the cation i,
  $\Gamma_S(\sigma_m)$ is activity coefficient for a segment with charge density $\sigma_m$ in solution S, and
  $\Gamma_i(\sigma_m)$ is activity coefficient for a segment with charge density $\sigma_m$ in cation i.

34. The computer apparatus of claim 32, wherein the activity coefficient for each respective anion of each electrolyte is represented by:

$$\ln \gamma_{i=anion/S}^{COSMO\text{-}SAC} = n_i \sum_{\sigma_m \in anion} p_i(\sigma_m)[\ln \Gamma_S(\sigma_m) - \ln \Gamma_i(\sigma_m)],$$

wherein
  $n_i$ is number of segments associated with anion i,
  $p_i(\sigma_m)$ is probability of a charge density o of the anion i
  $\Gamma_S(\sigma_m)$ is activity coefficient for a segment with charge density $\sigma_m$ in solution S, and
  $\Gamma_i(\sigma_m)$ is activity coefficient for a segment with charge density $\sigma_m$ in anion i.

35. The computer apparatus of claim 32, wherein the long range interaction contribution is represented by:

$$\ln \gamma_i^{PDH} = \frac{1}{RT}\left(\frac{\partial G^{ex,PDH}}{\partial n_i}\right)_{T,P,n_{j\neq i}} \; i,j = \text{solvent, ion}$$

wherein
  $\ln \gamma_i^{PDH}$=natural logarithm of activity coefficient of component i calculated from symmetric Pitzer-Debye-Hückel contribution R is gas constant,
T is temperature, and
$G^{ex,PDH}$ is excess Gibbs free energy due to long range ion-ion interactions.

36. The computer apparatus of claim 19, wherein mean activity coefficient for each electrolyte is represented by:

$$\ln\gamma_{\pm,i/S}^{COSMO-SAC} = \frac{1}{\nu}(\nu_c \ln\gamma_{i=cation/S}^{COSMO-SAC} + \nu_a \ln\gamma_{i=anion/S}^{COSMO-SAC}),$$

wherein
- $\gamma_{i=cation/S}^{COSMO-SAC}$ is activity coefficient of each respective cation for the electrolyte,
- $\gamma_{i=anion/S}^{COSMO-SAC}$ is activity coefficient of each respective anion for the electrolyte,
- $\nu_c$ is cationic stoichiometric coefficient,
- $\nu_a$ is anionic stoichiometric coefficient, and
- $\nu = \nu_c + \nu_a$.

* * * * *